(12) United States Patent
Colman et al.

(10) Patent No.: US 10,300,234 B2
(45) Date of Patent: May 28, 2019

(54) ENDOSCOPIC BITE BLOCK

(71) Applicant: ORIDION MEDICAL 1987 LTD., Jerusalem (IL)

(72) Inventors: Joshua Lewis Colman, Jerusalem (IL); Gershon Levitsky, Jerusalem (IL); Ron Porat, D.N. Huelu (IL)

(73) Assignee: ORIDION MEDICAL 1987 LTD., Hotzvim, Jerusalem (IL)

(*) Notice: Subject to any disclaimer, the term of this patent is extended or adjusted under 35 U.S.C. 154(b) by 175 days.

(21) Appl. No.: 15/610,279

(22) Filed: May 31, 2017

(65) Prior Publication Data

US 2017/0333656 A1    Nov. 23, 2017

Related U.S. Application Data

(63) Continuation of application No. 15/212,956, filed on Jul. 18, 2016, now Pat. No. 9,687,623, which is a
(Continued)

(51) Int. Cl.
| | |
|---|---|
| *A61B 1/00* | (2006.01) |
| *A61B 1/24* | (2006.01) |
| *A61B 5/08* | (2006.01) |
| *A61B 1/267* | (2006.01) |
| *A61B 1/273* | (2006.01) |

(Continued)

(52) U.S. Cl.
CPC ..... *A61M 16/0493* (2014.02); *A61B 1/00147* (2013.01); *A61B 1/00154* (2013.01); *A61B 1/24* (2013.01); *A61B 1/2676* (2013.01); *A61B 1/2736* (2013.01); *A61B 5/082* (2013.01); *A61B 5/097* (2013.01); *A61M 16/0488* (2013.01); *A61M 16/0497* (2013.01); *A61M 16/0666* (2013.01); *A61M 16/0672* (2014.02); *A61M 16/0683* (2013.01); *A61M 16/085* (2014.02); *A61M 16/0875* (2013.01); *A61M 16/20* (2013.01); *A61M 39/22* (2013.01); *A61M 16/0833* (2014.02); *A61M 2016/0413* (2013.01);
(Continued)

(58) Field of Classification Search
None
See application file for complete search history.

(56) References Cited

U.S. PATENT DOCUMENTS

| | | |
|---|---|---|
| 4,989,599 A | 2/1991 | Carter et al. |
| 5,046,491 A | 9/1991 | Derrick et al. |

(Continued)

FOREIGN PATENT DOCUMENTS

| | | |
|---|---|---|
| WO | 2004030723 A2 | 4/2004 |
| WO | 2004103199 A2 | 12/2004 |
| WO | 2005016142 A1 | 2/2005 |

OTHER PUBLICATIONS

EP05812952 European Search Report dated Jul. 1, 2010.
(Continued)

*Primary Examiner* — Sundhara M Ganesan
(74) *Attorney, Agent, or Firm* — Fletcher Yoder PC

(57) ABSTRACT

According to a preferred embodiment of the present invention there is provided a bite block assembly adapted for capnography and oxygen delivery to a subject, the bite block assembly (50) including a first capnography passageway adapted for passage therethrough of exhaled breath from the subject to a capnograph and a second oxygen delivery passageway, separate from the first passageway, adapted for passage therethrough of oxygen from an oxygen source to the mouth of the subject.

20 Claims, 21 Drawing Sheets

Related U.S. Application Data continuation of application No. 14/719,308, filed on May 21, 2015, now Pat. No. 9,867,957, which is a continuation of application No. 14/292,811, filed on May 30, 2014, now Pat. No. 9,060,680, which is a continuation of application No. 13/968,737, filed on Aug. 16, 2013, now Pat. No. 8,770,189, which is a continuation of application No. 12/085,594, filed as application No. PCT/IL2005/001291 on Dec. 1, 2005, now Pat. No. 8,534,278.

(51) Int. Cl.
| | | |
|---|---|---|
| *A61B 5/097* | (2006.01) | |
| *A61M 16/04* | (2006.01) | |
| *A61M 16/06* | (2006.01) | |
| *A61M 16/08* | (2006.01) | |
| *A61M 16/20* | (2006.01) | |
| *A61M 39/22* | (2006.01) | |

(52) U.S. Cl.
CPC .............. *A61M 2202/0208* (2013.01); *A61M 2230/432* (2013.01)

(56) References Cited

U.S. PATENT DOCUMENTS

| | | |
|---|---|---|
| 5,174,284 A | 12/1992 | Jackson et al. |
| 5,273,032 A | 12/1993 | Borody et al. |
| 5,335,656 A | 8/1994 | Bowe et al. |
| 5,413,095 A | 5/1995 | Weaver et al. |
| 5,480,410 A | 1/1996 | Cuschieri et al. |
| 5,513,634 A | 5/1996 | Jackson et al. |
| 5,699,787 A | 12/1997 | Thompson et al. |
| 5,752,510 A | 5/1998 | Goldstein et al. |
| 6,257,238 B1 | 7/2001 | Meah |
| 6,379,312 B2 | 4/2002 | O'Toole |
| 6,422,240 B1 | 7/2002 | Levitsky et al. |
| 6,561,192 B2 | 5/2003 | Palmer |
| 6,792,943 B2 | 9/2004 | Kumar et al. |
| 6,805,126 B2 | 10/2004 | Dutkiewicz |
| 7,624,736 B2 | 12/2009 | Borody |
| 7,727,194 B2 | 6/2010 | Nalagatla et al. |
| 7,832,400 B2 | 11/2010 | Curti et al. |
| 7,946,288 B2 | 5/2011 | Flynn et al. |
| 2004/0129272 A1 | 7/2004 | Ganesh et al. |
| 2004/0129273 A1 | 7/2004 | Hickle |
| 2007/0006878 A1 | 1/2007 | Mackey et al. |
| 2007/0068535 A1 | 3/2007 | Colman et al. |
| 2007/0113844 A1 | 5/2007 | Garren et al. |
| 2010/0262033 A1 | 10/2010 | Colman et al. |

OTHER PUBLICATIONS

International Search Report for PCT/IL05/01291 dated May 24, 2007.
International Search Report for PCT/IL04/00430 dated Mar. 4, 2005.

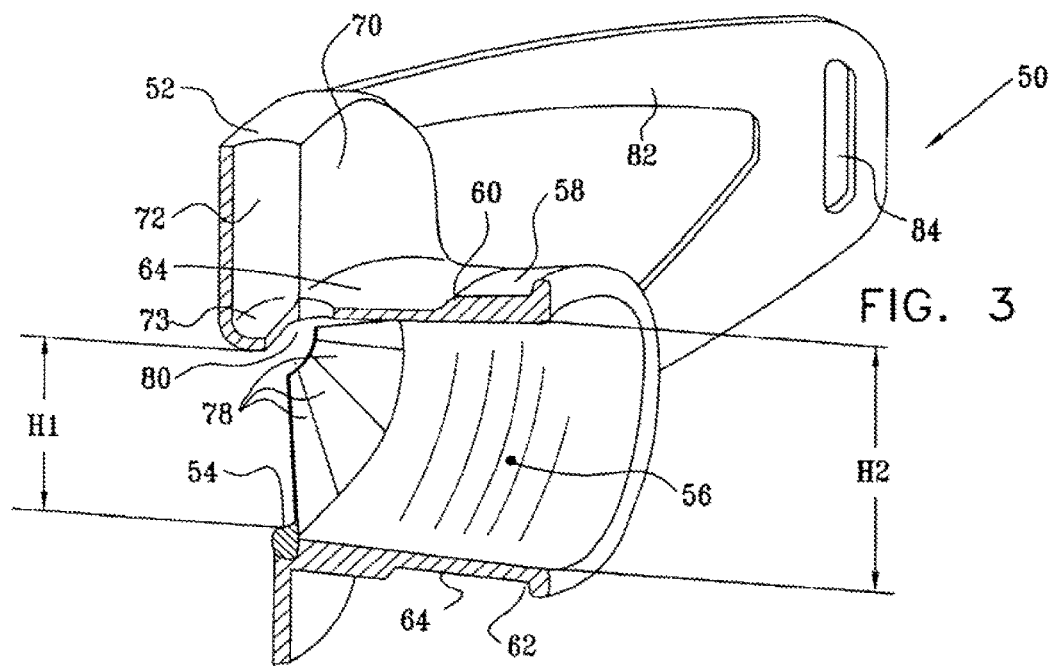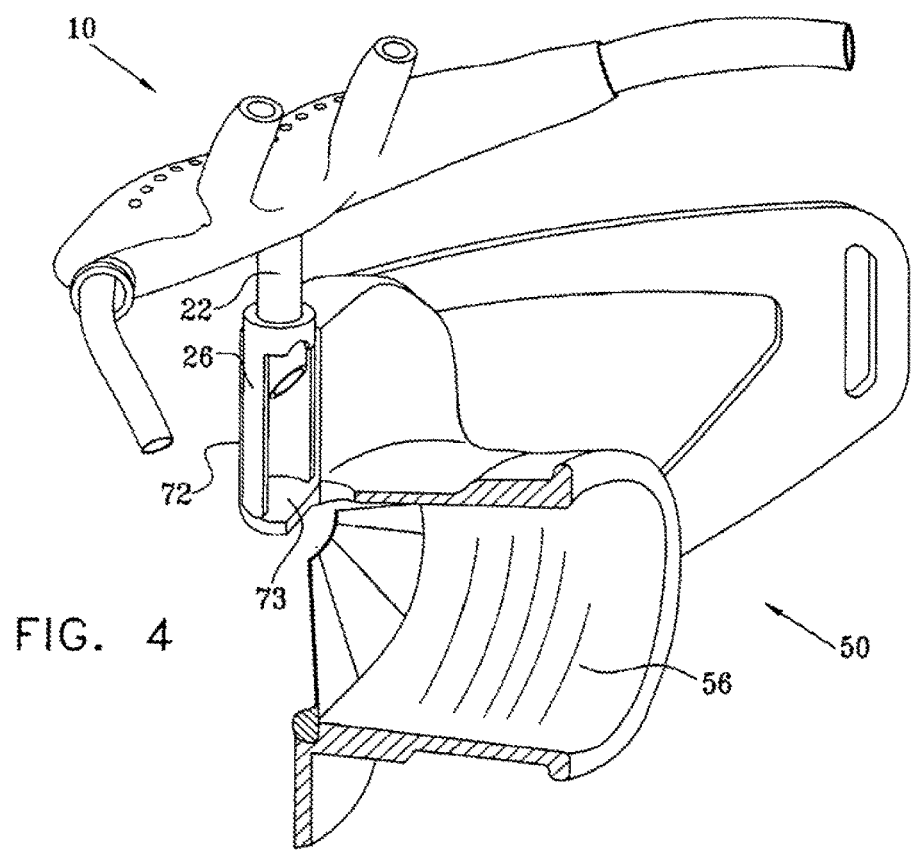

ENDOSCOPIC BITE BLOCK

This application is a continuation of U.S. application Ser. No. 15/212,956 filed Jul. 18, 2016, which is a continuation of U.S. application Ser. No. 14/719,308, filed May 21, 2015, which is a continuation of U.S. Pat. No. 9,060,680, filed May 30, 2014, which is a continuation of U.S. U.S. Pat. No. 8,770,189, filed Aug. 16, 2013, which is a continuation of U.S. Pat. No. 8,534,278, filed May 28, 2008, which is a National Stage Application that claims priority from and the benefit of International Application No. PCT/IL2005/001291, filed Dec. 1, 2005. Each of the foregoing applications is hereby incorporated by reference in its entirety for all purposes.

REFERENCE TO RELATED APPLICATIONS

Reference is made to PCT Patent Application PCT/IL2004/000430, filed May 20, 2004, entitled "ENDOSCOPIC BITE BLOCK", the disclosure of which is hereby incorporated herein by reference.

FIELD OF THE INVENTION

The present invention relates to the field of bite blocks for endoscopic use and specifically to endoscopic bite blocks suitable for use with gas sampling or delivery cannulae.

BACKGROUND OF THE INVENTION

The following U.S. Patents are believed to represent the current state of the art: U.S. Pat. Nos. 5,174,284; 6,257,238; 6,422,240; 5,273,032 and 5,513,634.

SUMMARY OF THE INVENTION

The present invention seeks to provide a new endoscopic bite block.

There is thus provided in accordance with a preferred embodiment of the present invention a bite block assembly adapted for capnography and oxygen delivery to a subject, the bite block assembly including a first capnography passageway adapted for passage therethrough of exhaled breath from the subject to a capnograph, and a second oxygen delivery passageway, separate from the first passageway, adapted for passage therethrough of oxygen from an oxygen source to the mouth of the subject.

Preferably the bite block assembly also includes a gas collection cannula having formed therein the first capnography passageway. Additionally the gas collection cannula also includes an oxygen delivery cannula adapted to deliver oxygen from the oxygen source to the nostrils of the subject. More preferably the oxygen delivery cannula is connected to the oxygen source by a gas delivery tube.

Preferably the bite block assembly also includes a bite block having formed therein the second oxygen delivery passageway.

More preferably the bite block assembly also includes a tube element adapted to connect the oxygen delivery cannula to the second oxygen delivery passageway. Additionally, the tube element includes a branch of the gas delivery tube, and is adapted to connect to the second oxygen delivery passageway. Additionally the tube element is sealed by a normally closed valve. Preferably the normally closed valve includes a luer valve. Additionally a mating luer portion of the luer valve is mounted onto the oxygen delivery passageway.

Preferably the tube element is permanently mounted onto the bite block and is adapted to connect to the gas delivery tube at a connection point formed therein. Additionally the connection point is sealed by a normally closed valve. Preferably the normally closed valve includes a luer valve. More preferably a mating luer portion of the luer valve is mounted onto the tube element.

There is thus provided in accordance with another preferred embodiment of the present invention, a capnography system including a capnograph, a bite block adapted to maintain the mouth of a subject open during a medical procedure, an exhaled breath sampling element which is connectable to the capnograph and mountable onto the bite block, and an oral oxygen delivery passageway which is connectable to the bite block for delivering oxygen from an oxygen source to the mouth of the subject.

Preferably the exhaled breath-sampling element has at least one gas collection passageway, formed therein, the gas collection passageway being configured to collect exhaled breath of the subject. Additionally the at least one gas collection passageway includes a nasal gas collection passageway configured for collecting breath exhaled through at least one nostril of the subject. Additionally or alternatively the at least one gas collection passageway includes an oral gas collection passageway configured for collecting breath exhaled through the mouth of the subject.

Preferably the capnography system also includes a nasal gas delivery passageway for delivering oxygen from the oxygen source to at least one nostril of the subject. Additionally the nasal gas delivery passageway is connected to the oxygen source by a gas delivery tube. More preferably the oral oxygen delivery passageway includes a tubular branch of the gas delivery tube.

Preferably the oral oxygen delivery passageway is sealed by a normally closed valve. Additionally the normally closed valve includes a luer valve. More preferably a mating luer portion of the luer valve is mounted onto the oral oxygen delivery passageway.

Preferably the oral oxygen delivery passageway is permanently mounted onto the bite block and is adapted to connect to the gas delivery tube at a connection point formed therein. Additionally the connection point is sealed by a normally closed valve. More preferably the normally closed valve includes a luer valve. Additionally a mating luer portion of the luer valve is mounted onto the oral oxygen delivery passageway.

BRIEF DESCRIPTION OF THE DRAWINGS

The present invention will be understood and appreciated more fully from the following detailed description, taken in conjunction with the drawings in which:

FIG. 3 is a simplified sectional pictorial illustration of the endoscopic bite block of FIGS. 2A and 2B, taken along sections lines in FIG. 2B;

FIG. 4 is a simplified schematic illustration of the connection between the oral nasal cannula of FIGS. 1A and 1B and the endoscopic bite block of FIGS. 2A-3;

DETAILED DESCRIPTION OF PREFERRED EMBODIMENTS

A bite block is a device commonly used during upper gastro-intestinal endoscopic procedures to facilitate passage of an esophago-gastro-duodenoscopy (EGD) endoscope. The purpose of the bite block is to allow the physician to perform the procedure without the subject interfering by biting and damaging the endoscope tubing inserted via his mouth, whether voluntarily or involuntarily.

The upper gastro-intestinal endoscopic procedure itself, together with the use of a bite block, is often highly uncomfortable for the subject and therefore it is very common for the subject to be sedated during the procedure. Despite this, it is common for the subject to show opposition to the procedure.

During upper gastro-intestinal endoscopy, and especially during long duration procedures performed under sedation, CO2 monitoring is often performed using a separate nasal or oral/nasal cannula in conjunction with a bite block. Concomitant use of bite blocks and cannulae may noticeably affect capnographic performance for a number of reasons, including inter alia misalignment between the cannula and the bite block and inefficient oral sampling due to the space taken up by the endoscope. The present invention provides a solution that generally does not affect the capnographic performance.

Figure 1A:
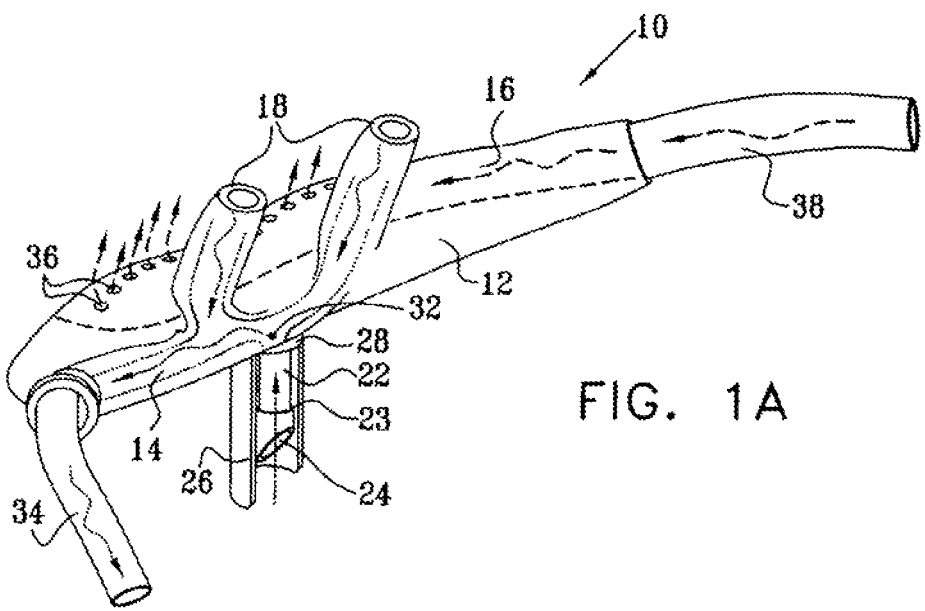
FIGS. 1A and 1B are simplified pictorial illustrations of an oral nasal sampling cannula forming part of an endoscopic bite block assembly, constructed and operative in accordance with a preferred embodiment of the present invention, in retracted and extended orientations respectively.
Figure 1B:
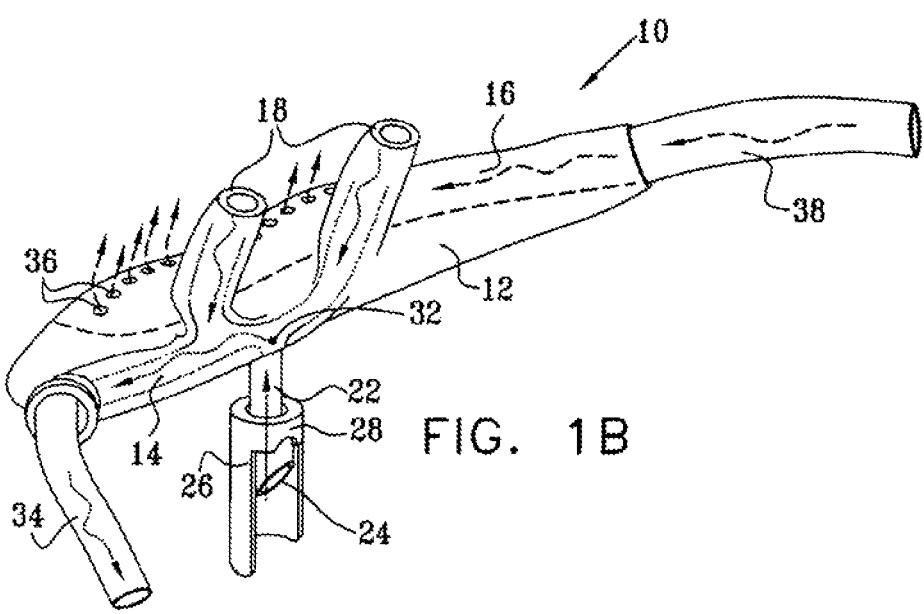

Reference is now made to FIGS. 1A and 1B, which are simplified pictorial illustrations of an oral nasal sampling cannula forming part of an endoscopic bite block assembly, constructed and operative in accordance with a preferred embodiment of the present invention, in retracted and extended orientations respectively.

FIGS. 1A and 1B show an oral nasal sampling cannula 10, which is adapted for collection of gases, such as carbon dioxide, exhaled by a subject, and for supplying oxygen to the subject.

The oral nasal sampling cannula 10 comprises a main body portion 12, having formed therein an exhaled breath collection bore 14 and an oxygen delivery bore 16. A pair of hollow nasal prongs 18, which are adapted for insertion into the nostrils of the subject, is integrally formed with the main body portion 12. A hollow oral prong 22, which is formed with a limiting rib 23 and a cut-away tip 24, is mounted onto a bottom surface of main body portion 12. An oral breath directing element 26, which is preferably in the shape of a cut-away tube, is slidably mounted onto oral prong 22 by a mounting portion 28, and positioning of the oral breath directing element 26 is limited by the limiting rib 23 of oral prong 22.

A channel formed in oral prong 22 is in fluid flow connection with channels formed in nasal prongs 18, thereby forming a single junction 32. Single junction 32 is in fluid flow communication with exhaled breath collection bore 14, which in turn is in fluid flow communication with an exhaled breath collection tube 34, which is adapted to be connected to a breath test analyzer or a capnograph (not shown), such as Microcap® which is commercially available from Oridion Medical LTD. of Jerusalem, Israel.

Main body portion 12 is formed with oxygen delivery openings 36, which are in fluid flow communication with oxygen delivery bore 16, which in turn is in fluid flow communication with an oxygen delivery tube 38. Alternatively, at least one nasal oxygen delivery prong, adapted for insertion into the subject's nostril, may be used instead of oxygen delivery openings 36. Oxygen delivery tube 38 is adapted to be connected to a source of oxygen (not shown).

Oxygen delivery tube 38 and exhaled breath collection tube 34 may optionally be placed around the ears of the subject, thereby stabilizing the oral nasal sampling cannula 10 on the subject's face, such that any movement of the subject will have a negligible effect on the placement of the oral nasal sampling cannula 10.

It is appreciated that oral breath directing element 26 may be in a retracted orientation as shown in FIG. 1A, or in an extended orientation as shown in FIG. 1B, thereby allowing the oral nasal sampling cannula 10 to be suited to the facial dimensions of the subject, resulting in more efficient collection of exhaled breath.

Figure 2A:
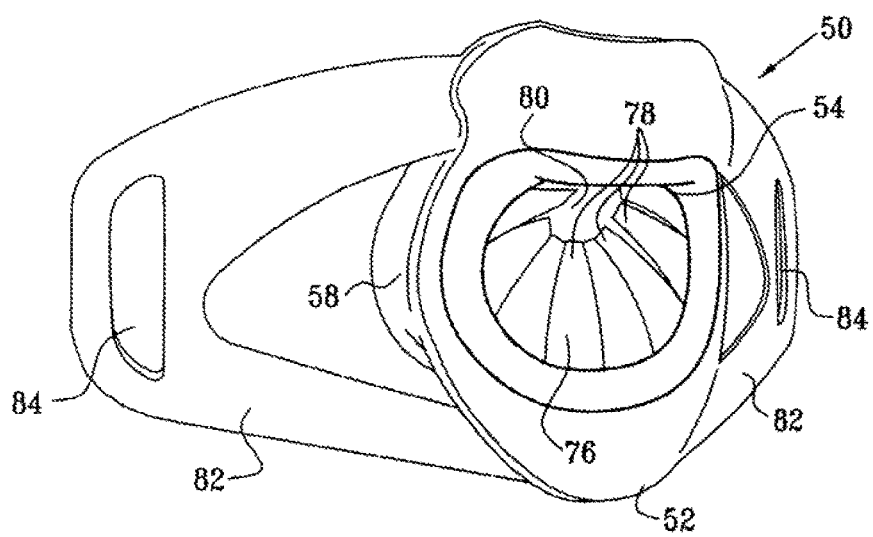
FIGS. 2A and 2B are front-view and rear-view simplified pictorial illustrations of an endoscopic bite block forming part of an endoscopic bite block assembly, constructed and operative in accordance with a preferred embodiment of the present invention.
Figure 2B:
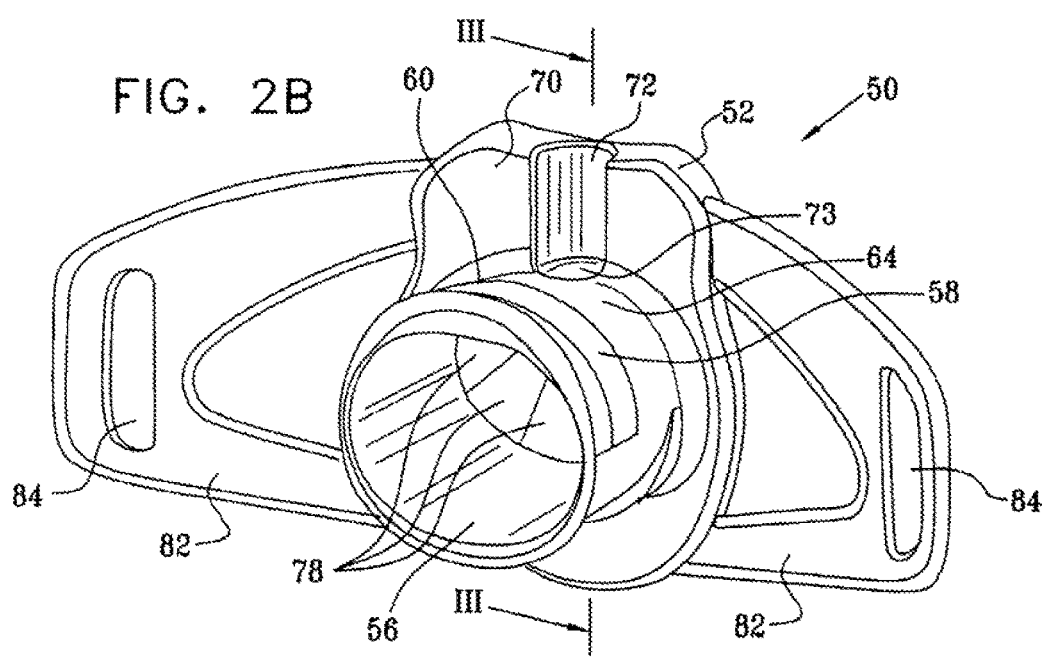

Reference is now made to FIGS. 2A and 2B, which are front-view and rear-view simplified pictorial illustrations of an endoscopic bite block forming part of an endoscopic bite block assembly constructed and operative in accordance with a preferred embodiment of the present invention and to FIG. 3, which is a simplified sectional pictorial illustration thereof.

FIGS. 2A, 2B and 3 show an endoscopic bite block 50, which is adapted to be inserted into the mouth of a subject while the subject is sedated, to ensure that the mouth of the subject is maintained open during the endoscopy process and that the subject does not interfere with the process by biting on the medical instruments used.

The endoscopic bite block 50 includes a main body portion 52, having formed therein a central opening 54. A hollow tubular portion 56 extends distally from main body portion 52, such that the opening of tubular portion 56 is an extension of central opening 54. Central opening 54 is of a first height, indicated by H1 in FIG. 3, which is typically 16 to 20 mm in bite blocks for adult use, which is the height required by medical personnel for performing an endoscopy. In order to ensure that during breath sampling, oral prong 22 of oral nasal sampling cannula 10 (FIGS. 1A and 1B) does not interfere with the space required by medical personnel for performing the endoscopy procedure, the height of tubular portion 56 is greater than the height H1 of the central opening 54 as indicated by H2 in FIG. 3, and is typically 2 to 4 mm more than height H1 (18 to 24 mm).

An outer surface 58 of tubular portion 56 is formed with top and bottom teeth engagement surfaces 60 and 62, such that top teeth engagement surface 60 is relatively forward of bottom teeth engagement surface 62. This structure facilitates easy and accurate biting of the bite block 50 by a subject, as it is suited to the jaw morphology of a closed human mouth. Surface 58 is additionally formed with jaw engagement recesses 64, which are formed forwardly of teeth engagement surfaces 60 and 62, respectively.

A top inner surface 70 of main body portion 52 is formed with a longitudinal groove 72 having a transverse surface 73, which is adapted to accommodate oral prong 22 and oral breath directing element 26 of the oral nasal sampling cannula 10 (FIGS. 1A and 1B), as described with more detail herein below with reference to FIG. 4.

A flexible barrier 76, preferably comprised of several flaps 78, is disposed within central opening 54, thereby substantially closing off the central opening and preventing dilution of exhaled breath by ambient air during sampling. An opening 80 is preferably maintained within flexible barrier 76, thereby ensuring a small part of central opening 54 remains open in order to enable the subject to inhale external air. The flexible barrier 76 ensures that a majority of the subject's orally exhaled breath will be directed toward oral prong 22 (FIGS. 1A and 1B) thereby ensuring accurate sampling of the subject's breath. Opening 80 is preferably placed at a top part of central opening 54 near the cut-away tip 24 of oral prong 22 (FIGS. 1A and 1B), thereby directing exhaled breath toward the oral prong 22 as it is the only substantial exit.

The flaps 78 are preferably formed of a plastic material selected to be of suitable thickness to maintain their position when undisturbed, yet bend readily when pushed by an endoscope probe, and thus do not limit the actions of the medical personnel performing the endoscopy. However, the flaps 78 preferably close back around the endoscope probe, thus maintaining a substantially closed oral cavity volume and allowing most of the exchange of gases to occur close to the opening 80 of the flexible barrier 76 which is close to the cut-away tip 24 of oral prong 22 (FIGS. 1A and 1B) from which capnographic sampling can be performed accurately. Additionally, the flaps 78 are preferably transparent, thus enabling medical personnel to see into the oral cavity during the endoscopy procedure.

Two attachment surfaces 82, each formed with a slit 84, extend horizontally outwardly from main body portion 52. Slits 84 are adapted to connect to a band which is placed around the subject's head and is used to maintain the endoscopic bite block 50 firmly in position during the endoscopy procedure. Preferably, slits 84 are located above a horizontal centerline of main body portion 52, such that the connected band will tend to exert a stronger pull to the top of the main body portion 52, thus assisting in overcoming the subject's tendency to tilt the bite block 50 outward during the endoscopy procedure and in maintaining the bite block 50 upright in the subject's mouth.

Reference is now made to FIG. 4, which is a simplified schematic illustration of the connection between the oral nasal sampling cannula of FIGS. 1A and 1B and the endoscopic bite block of FIGS. 2A-3.

As seen in FIG. 4, oral prong 22 of oral nasal sampling cannula 10 is accommodated within groove 72 of bite block 50, such that a bottom surface of oral breath directing element 26 engages transverse surface 73 of the groove 72. It is appreciated that transverse surface 73 is located below an inner surface of tubular portion 56 in order to ensure that air exhaled by the subject into tubular portion 56 will be directed toward groove 72 and oral prong 22.

Reference is now made to FIGS. 5A, 5B, 5C, 5D, 5E, 5F and 5G, which are pictorial illustrations of various stages of typical use of the endoscopic bite block assembly of FIGS. 1A-4.

Figure 5A:
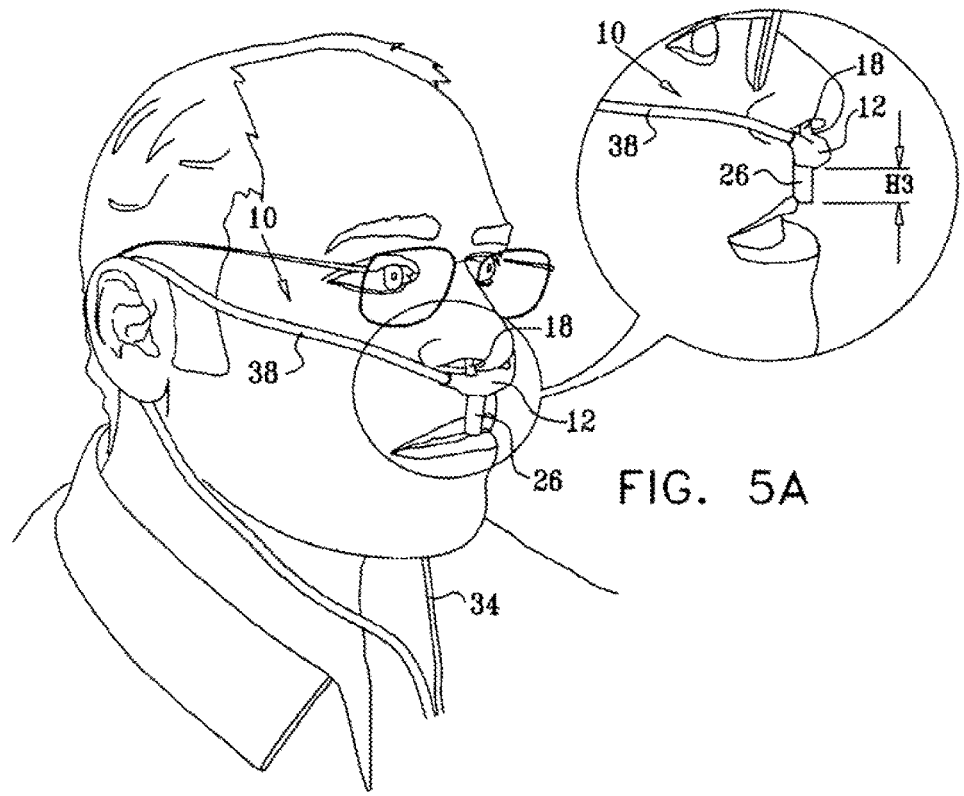
FIGS. 5A, 5B, 5C, 5D, 5E, 5F and 5G are pictorial illustrations of various stages of typical use of the endoscopic bite block assembly of FIGS. 1A-4.

As seen in FIG. 5A, the nasal prongs 18 of the oral nasal sampling cannula 10 are placed in the subjects nostrils, preferably before the subject is sedated. Preferably, the exhaled breath collection tube 34 and the oxygen delivery tube 38 are placed around the subject's ears, in order to ensure the stability of the oral nasal sampling cannula 10 on the subject's face. As seen in the enlarged portion of FIG. 5A, at this stage the oral breath-directing element 26 is in its retracted orientation, indicated by the length H3.

Figure 5B:
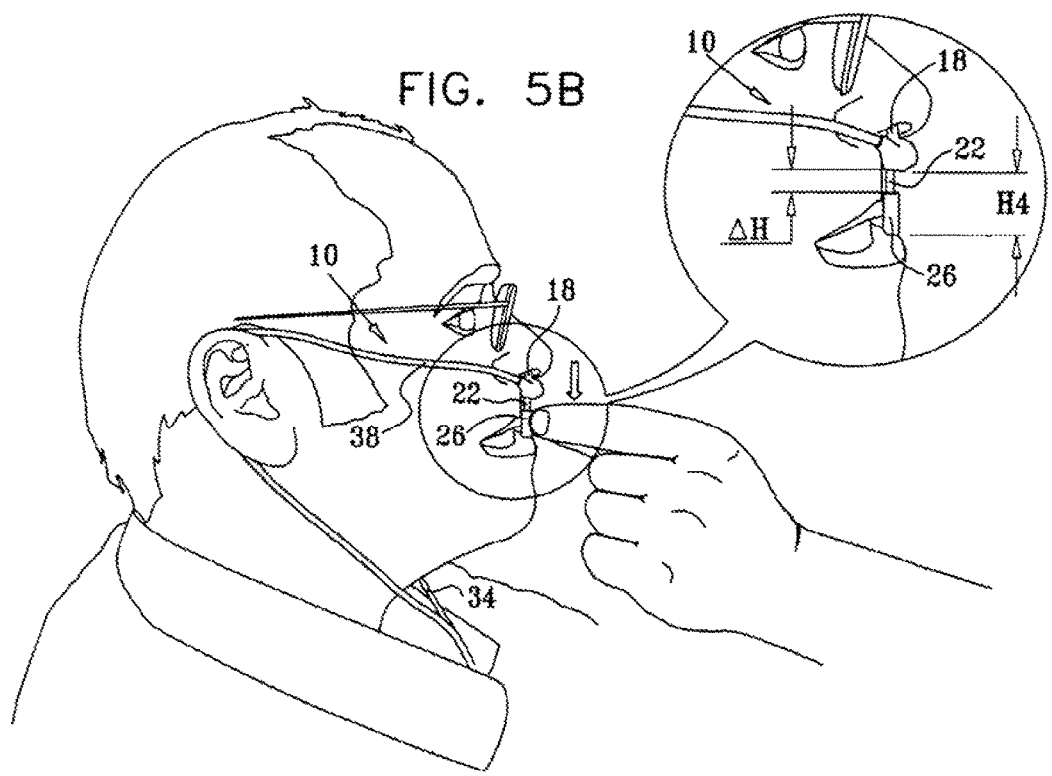

Turning to FIG. 5B, it is seen that the oral breath directing element 26 is extended to accommodate the facial dimensions of the subject, revealing part of oral prong 22. Preferably, the oral breath-directing element is moved down to a point in which a bottom end thereof is at the height of the top of the bottom lip of the subject, its new length being indicated by H4. This action is preferably preformed by medical personnel, but may alternatively be performed by the subject himself, a family member, or any other person.

Figure 5C:
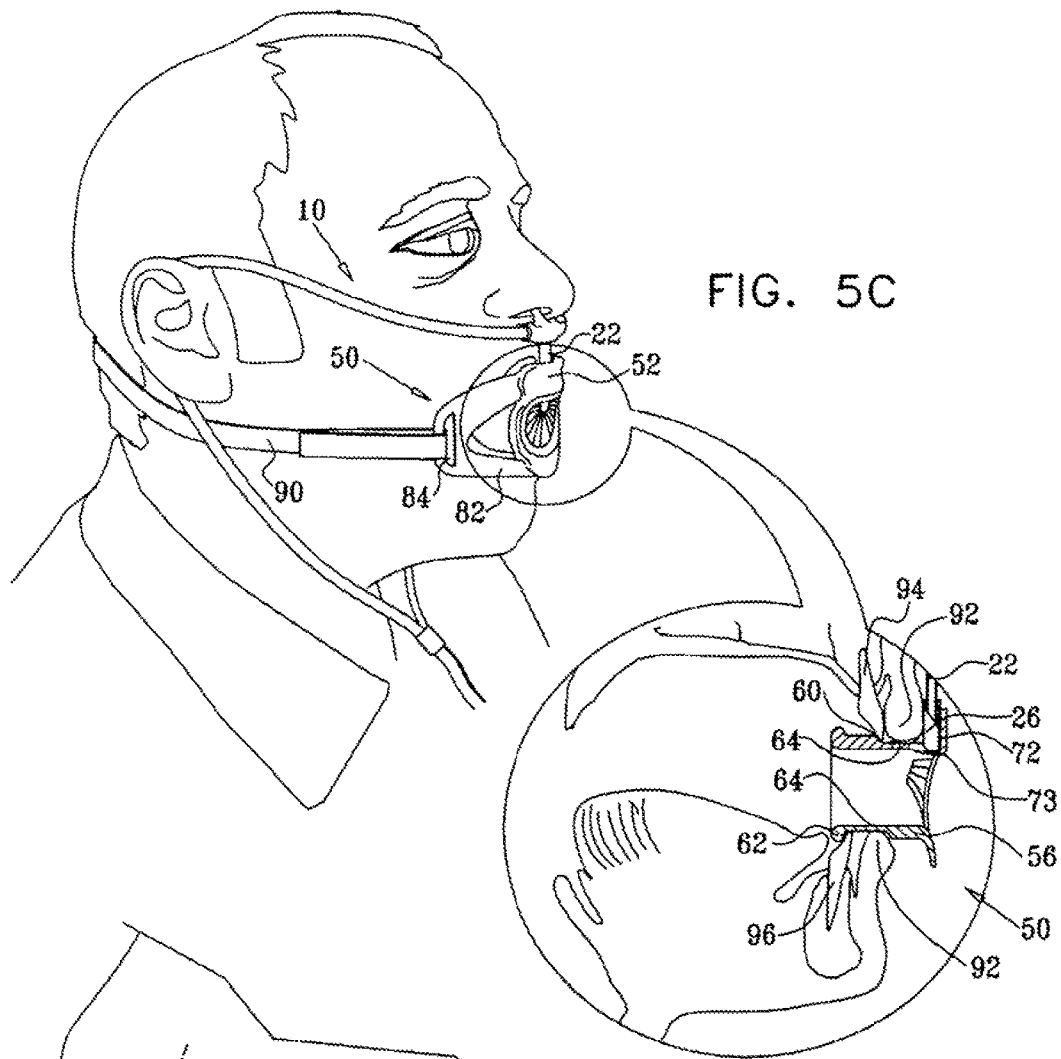

FIG. 5C illustrates the insertion of bite block 50 into the mouth of the subject, such that main body portion 52 engages the outer surface of the subject's lips and the tubular portion 56 is inside the subject's mouth. A strap, indicated by reference numeral 90, is attached to slits 84 of attachment surfaces 82 and is placed around the subject's head, thereby securing the bite block 50 in place. This stage is preferably performed when the subject is sedated, but may alternatively be performed prior thereto.

As seen in the enlarged portion of FIG. 5C, the oral breath directing element 26 and the oral prong 22 are accommodated in groove 72, such that a bottom surface of the oral breath directing element 26 engages transverse surface 73 of groove 72. Additionally, if oral breath directing element 26 has been extended more than necessary for the facial features of the subject, the transverse surface 73 pushes the oral breath-directing element 26 back, until it is optimally positioned. The lips of the subject, indicated by reference numeral 92 preferably engage jaw engagement recesses 64, and the top and bottom teeth of the subject, indicated by reference numerals 94 and 96 engage top and bottom teeth engagement surfaces 60 and 62, respectively.

Figure 5D:
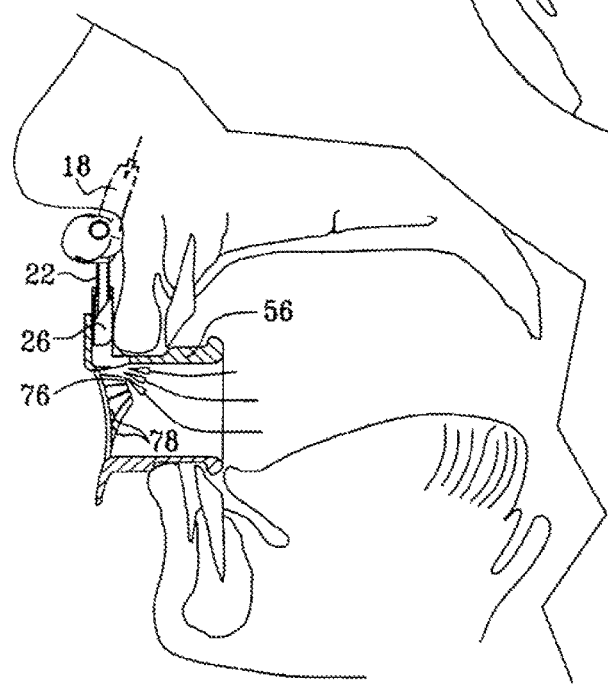

Turning to FIG. 5D, it is seen that air exhaled orally by the subject, indicated by arrows, passes through the bore of tubular portion 56, and is directed toward oral breath directing element 26 and oral prong 22 by the flaps 78 of flexible barrier 76. Air that is exhaled nasally by the subject passes through nasal prongs 18.

Figure 5E:
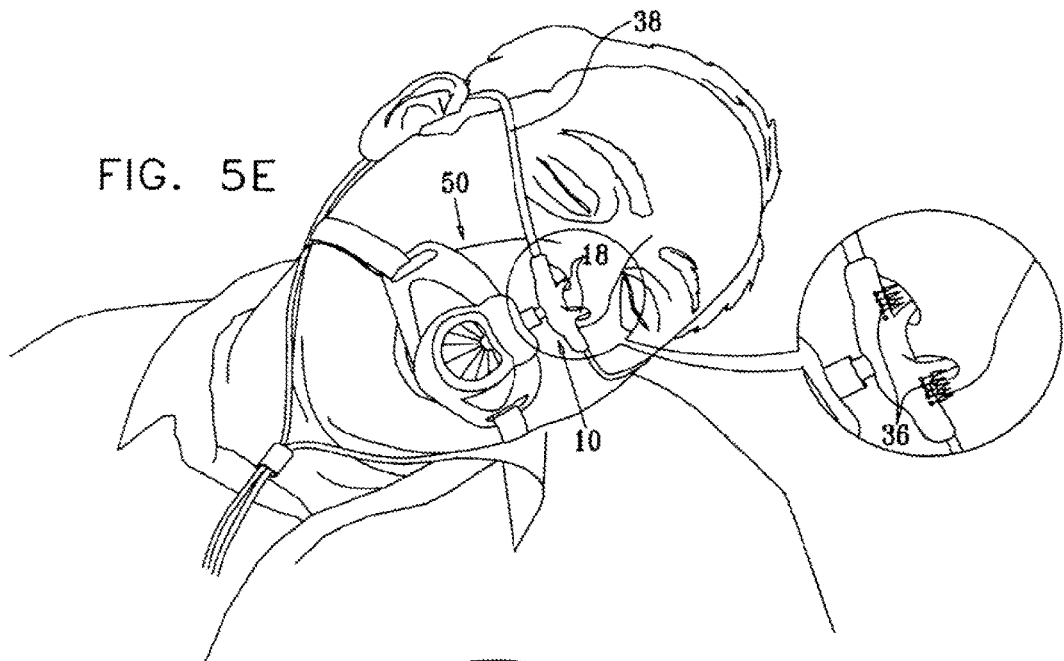

FIG. 5E illustrates the sedated subject, having the nasal prongs 18 of the oral nasal sampling cannula 10 in his nostrils and the endoscopic bite block 50 placed in his mouth and strapped to his head. Preferably, once the subject is sedated, oxygen is supplied to the nose of the subject via oxygen delivery openings 36 of oral nasal sampling cannula 10, as indicated by arrows in the enlarged portion of FIG. 5E. The oxygen is supplied to oxygen delivery openings 36 via oxygen delivery bore 16 (FIGS. 1A and 1B) and oxygen delivery tube 38.

Figure 5F:
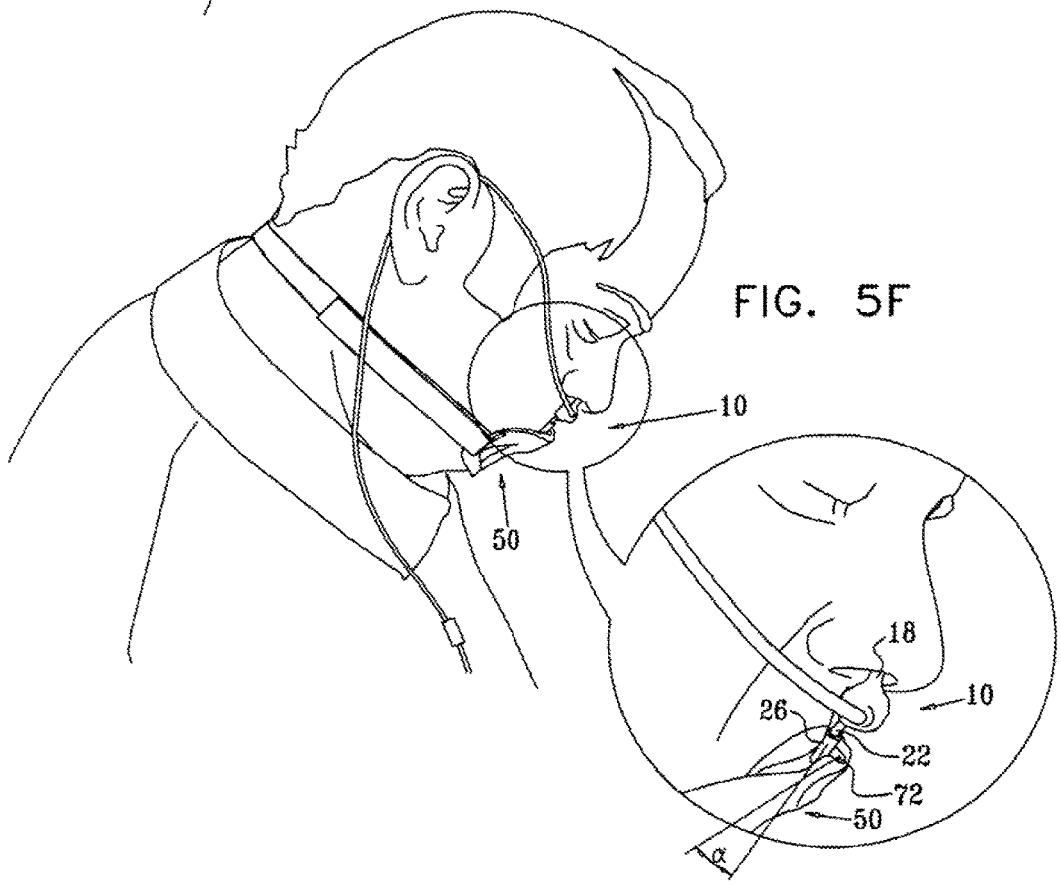

Turning to FIG. 5F, it is seen that when the subject is sedated, he tends to move or slump his head, thereby moving oral nasal sampling cannula 10 relative to bite block 50, as indicated by angle a in the enlarged portion of FIG. 5F. The feature of the present invention which provides oral nasal sampling cannula 10 which is physically separated from bite block 50 and the placement of oral breath directing element 26 and oral prong 22 within groove 72, ensure that even when the subject moves or slumps his head, the oral prong 22 and nasal prongs 18 will be maintained in their respective places, and accurate sampling will continue. Additionally, the placement of oral prong 22 within groove 72 provides a counter force to force applied by the subject's tongue to push at least the top portion of the bite block 50 out of the subject's mouth, thus ensuring accurate placement of the bite block.

Figure 5G:
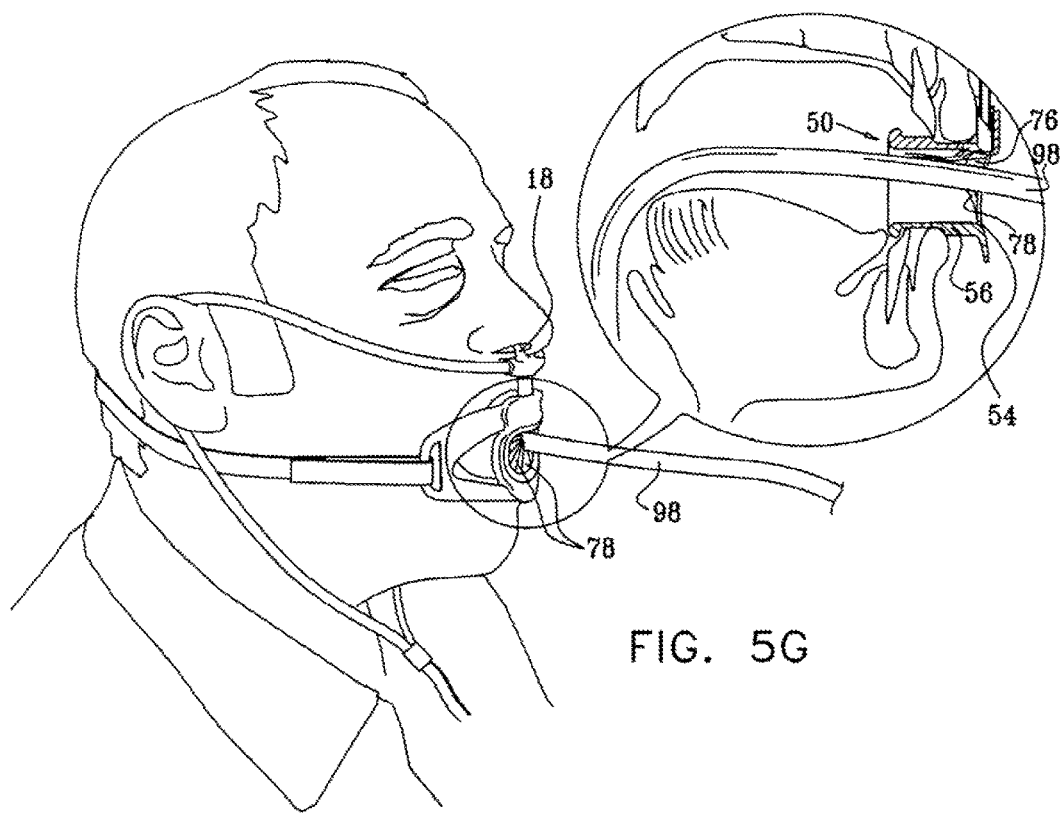

As seen in FIG. 5G, an endoscope probe 98 is inserted into the bore of tubular portion 56 of bite block 50, for performing an endoscopy procedure. During the insertion of endoscope probe 98 and its presence in the subject's mouth and pharynx, flaps 78 of flexible barrier 76 bend slightly inward to allow the passage of the endoscope probe 98, as seen with particular clarity in the enlarged portion of FIG. 5G. However, the central opening 54 of bite block 50 remains substantially closed by flaps 78, thereby separating the exhaled breath of the subject which is in the bore of tubular portion 56 from the ambient air.

Additionally, the sampling may continue during the presence of the endoscope probe 98 in the pharynx of the subject, as the tubular portion 56 is of a slightly larger diameter than the central opening 54, thereby ensuring that medical personnel have the space required for the endoscopy procedure and sampling can take place from the space defined by the difference between heights H2 and H1 (FIG. 3), as indicated by arrows in the enlarged portion of FIG. 5G.

It is appreciated that following the endoscopy, the bite block 50 may be removed from the subject's mouth, preferably by medical personnel. However, the sampling of exhaled breath through nasal prongs 18 which remain in the subject's nostrils and through oral prong 22 which remains near the subject's mouth, preferably continues until the subject has awaken from the sedation. This is necessary because the subject's breath must be monitored as long as the subject is sedated.

Figure 6A:
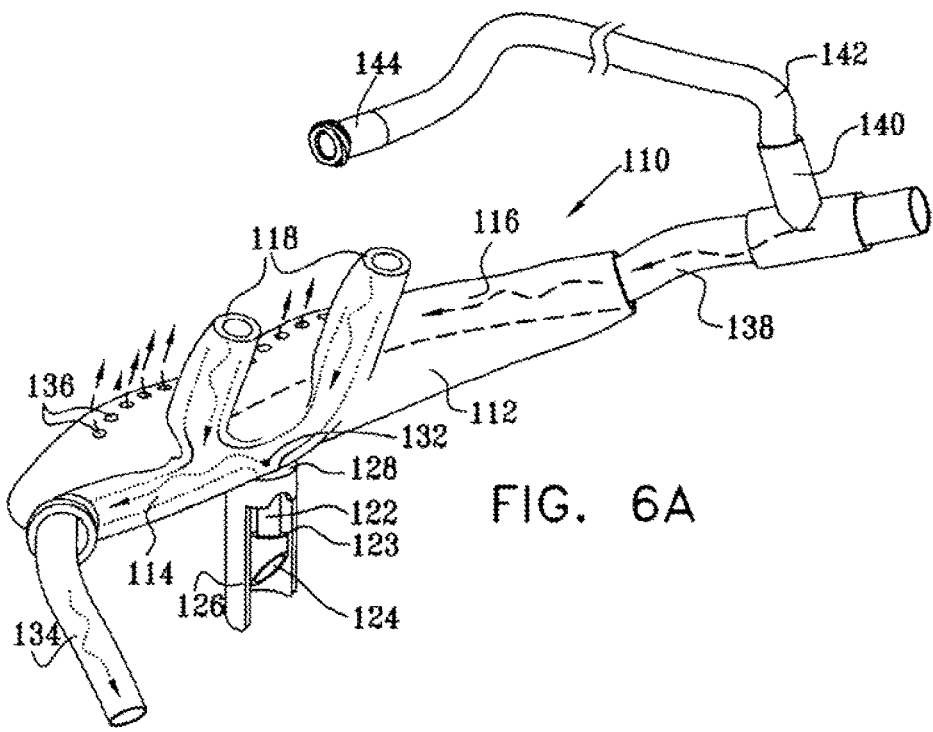
FIGS. 6A and 6B are simplified pictorial illustrations of an oral nasal cannula forming part of an endoscopic bite block assembly, constructed and operative in accordance with another preferred embodiment of the present invention, in retracted and extended orientations respectively.
Figure 6B:
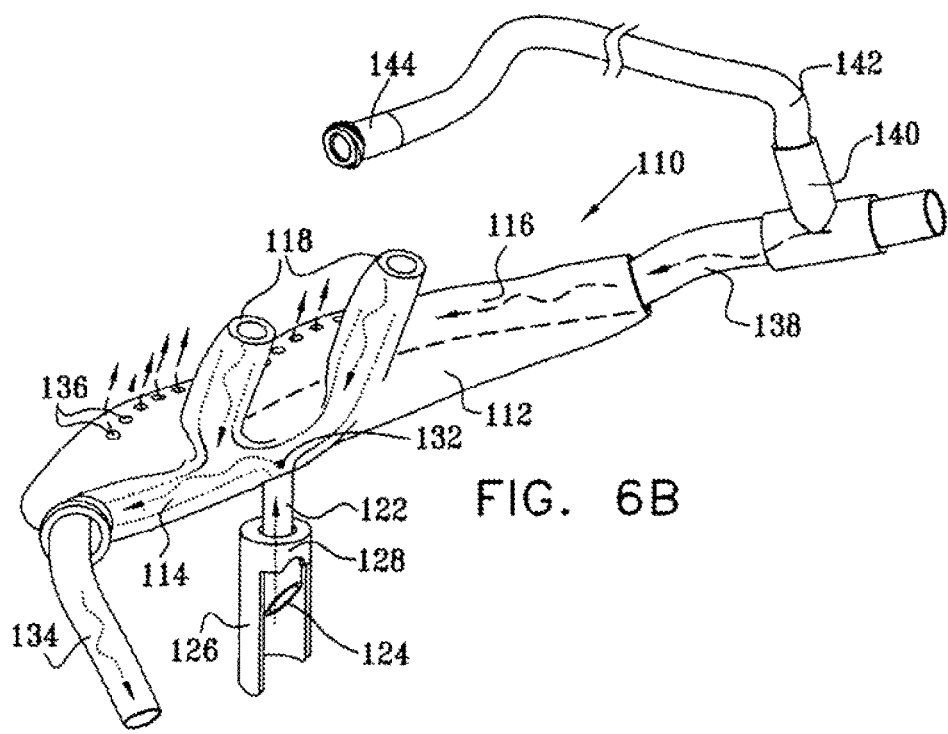

Reference is now made to FIGS. 6A and 6B, which are simplified pictorial illustrations of an oral nasal sampling cannula forming part of an endoscopic bite block assembly, constructed and operative in accordance with another preferred embodiment of the present invention, in retracted and extended orientations respectively.

FIGS. 6A and 6B show an oral nasal sampling cannula 110, which is adapted for collection of gases, such as carbon dioxide, exhaled by a subject, and for supplying oxygen to the subject.

The oral nasal sampling cannula 110 comprises a main body portion 112, having formed therein an exhaled breath collection bore 114 and an oxygen delivery bore 116. A pair of hollow nasal prongs 118, which are adapted for insertion into the nostrils of the subject, is integrally formed with the main body portion 112. A hollow oral prong 122, which is formed with a limiting rib 123 and a cut-away tip 124, is mounted onto a bottom surface of main body portion 112. An oral breath directing element 126, which is preferably in the shape of a cut-away tube, is slidably mounted onto oral prong 122 by a mounting portion 128, and positioning of the oral breath directing element 126 is limited by the limiting rib 123 of oral prong 122.

A channel formed in oral prong 122 is in fluid flow connection with channels formed in nasal prongs 118, thereby forming a single junction 132. Single junction 132 is in fluid flow communication with exhaled breath collection bore 114, which in turn is in fluid flow communication with an exhaled breath collection tube 134, which is adapted to be connected to a breath test analyzer or a capnograph (not shown), such as Microcap® which is commercially available from Oridion Medical LTD. of Jerusalem, Israel.

Main body portion 112 is formed with oxygen delivery openings 136, which are in fluid flow communication with oxygen delivery bore 116, which in turn is in fluid flow communication with an oxygen delivery tube 138. Alternatively, at least one nasal oxygen delivery prong, which is adapted to be inserted into the nostril of the subject, may be used instead of oxygen delivery openings 136. Oxygen delivery tube 138 is preferably formed with a T-element 140, connecting the oxygen delivery tube 138 to an oral oxygen delivery tube 142. Oxygen delivery tube 138 is adapted to be connected to a source of oxygen (not shown). Oral oxygen delivery tube 142 is preferably normally closed by a valve element 144. Typically, the valve is a luer type valve.

Oxygen delivery tube 138 and exhaled breath collection tube 134 may optionally be placed around the ears of the subject, thereby stabilizing the oral nasal sampling cannula 110 on the subject's face, such that any movement of the subject will have negligible effect on the placement of the oral nasal sampling cannula 110.

It is appreciated that oral breath directing element 126 may be in a retracted orientation as shown in FIG. 6A, or in an extended orientation as shown in FIG. 6B, thereby allowing the oral nasal sampling cannula 110 to be suited to the facial dimensions of the subject, resulting in more efficient collection of exhaled breath.

Figure 7A:
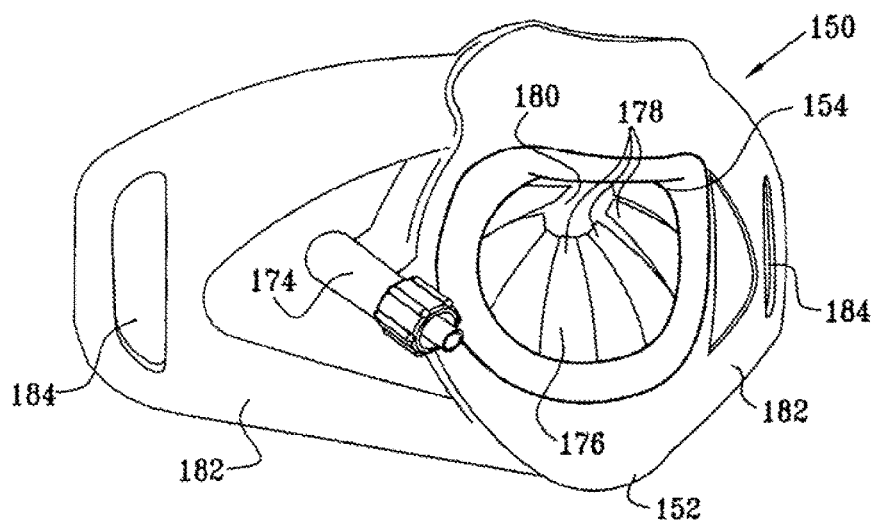
FIGS. 7A and 7B are front-view and rear-view simplified pictorial illustrations of an endoscopic bite block forming part of an endoscopic bite block assembly, constructed and operative in accordance with another preferred embodiment of the present invention.
Figure 7B:
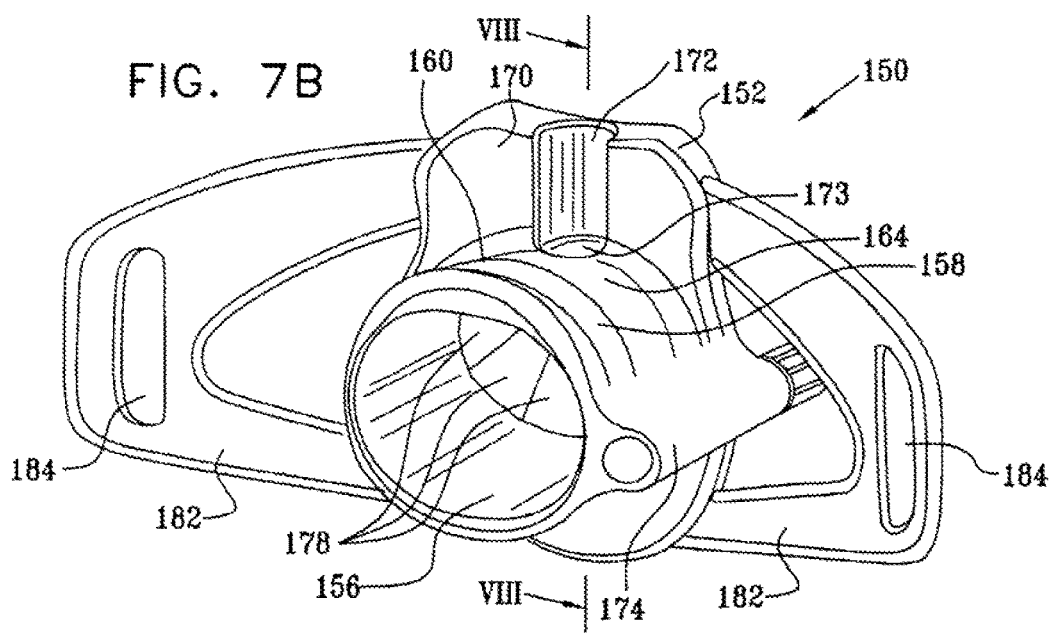
Figure 8:
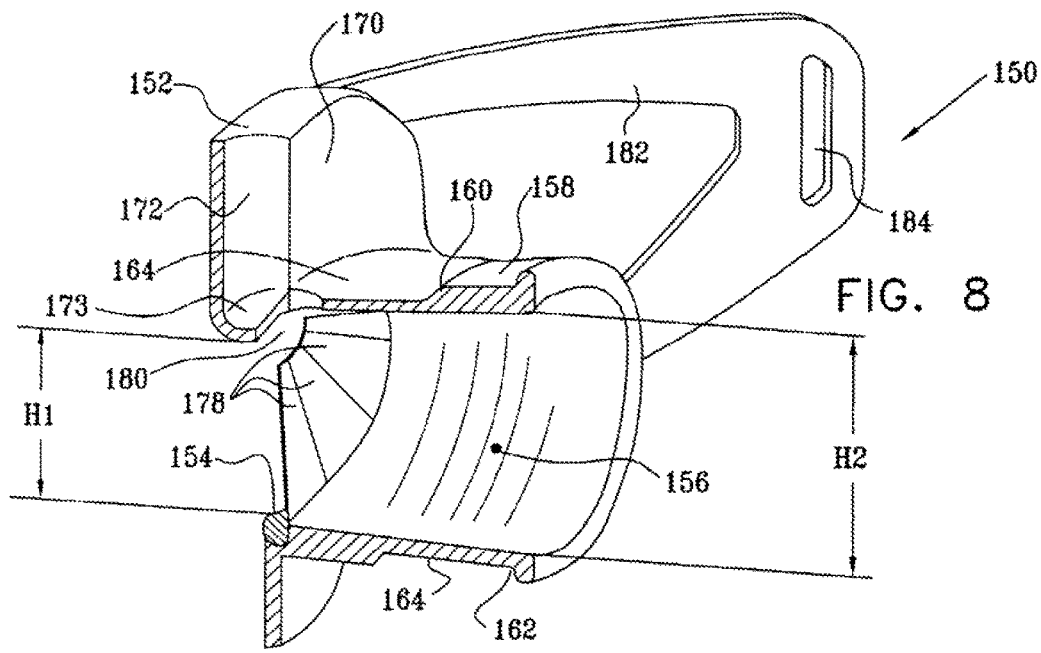
FIG. 8 is a simplified sectional pictorial illustration of the endoscopic bite block of FIGS. 7A and 7B, taken along sections lines VIII-VIII in FIG. 7B.

Reference is now made to FIGS. 7A and 7B, which are front-view and rear-view simplified pictorial illustrations of an endoscopic bite block forming part of an endoscopic bite block assembly constructed and operative in accordance with a preferred embodiment of the present invention and to FIG. 8, which is a simplified sectional pictorial illustration thereof.

FIGS. 7A, 7B and 8 show an endoscopic bite block 150, which is adapted to be inserted into the mouth of a subject while the subject is sedated, to ensure that the mouth of the subject is maintained open during the endoscopy process and that the subject does not interfere with the process by biting on the medical instruments used.

The endoscopic bite block 150 includes a main body portion 152, having formed therein a central opening 154. A hollow tubular portion 156 extends distally from main body portion 152, such that the opening of tubular portion 156 is an extension of central opening 154. Central opening 154 is of a first height, indicated by H1 in FIG. 8, which is typically 16 to 20 mm in bite blocks for adult use, which is the height required by medical personnel for performing an endoscopy. In order to ensure that during breath sampling, oral prong 122 of oral nasal sampling cannula 110 (FIGS. 6A and 6B) does not interfere with the space required by medical personnel for performing the endoscopy procedure, the height of tubular portion 156 is greater than the height H1 of central opening 154 as indicated by H2 in FIG. 8, and is typically 2 to 4 mm more than height H1 (18 to 24 mm).

An outer surface 158 of tubular portion 156 is formed with top and bottom teeth engagement surfaces 160 and 162, such that top teeth engagement surface 160 is relatively forward of bottom teeth engagement surface 162. This structure facilitates easy and accurate biting of the bite block 150 by a subject, as it is suited to the jaw morphology of a closed human mouth. Surface 158 is additionally formed with jaw engagement recesses 164, which are formed forwardly of teeth engagement surfaces 160 and 162, respectively.

A top inner surface 170 of main body portion 152 is formed with a longitudinal groove 172 having a transverse surface 173, which is adapted to accommodate oral prong 122 and oral breath directing element 126 of the oral nasal sampling cannula 110 (FIGS. 6A and 6B), as described with more detail hereinbelow with reference to FIG. 9.

A tubular portion 174 is formed on a side of outer surface 158 of tubular portion 156. Tubular portion 174 is adapted to threadably engage oral oxygen delivery tube 142 (FIGS. 6A and 6B), thereby opening valve 144 to the passage of gases and thus supplying oxygen directly to the oral cavity of the subject. Preferably, tubular portion 174 includes a luer portion corresponding to luer valve element 144. It is appreciated that tubular portion 174 is formed on outer surface 158 of tubular portion 156, in order to ensure that the oral oxygen delivery does not interfere with the procedure performed by the medical personnel and so that the oxygen flow does not directly interfere with the CO2 sampling.

A flexible barrier 176, preferably comprised of several flaps 178, is disposed within central opening 154, thereby substantially closing off the central opening and preventing dilution of exhaled breath by ambient air during sampling. An opening 180 is preferably maintained within flexible barrier 176, thereby ensuring a small part of central opening 154 to remain open in order to enable the subject to inhale external air. The flexible barrier 176 ensures that a majority of the subject's orally exhaled breath will be directed toward oral prong 122 (FIGS. 6A and 6B) thereby ensuring accurate sampling of the subject's breath. Opening 180 is preferably placed at a top part of central opening 154 near the cut-away tip 124 of oral prong 122 (FIGS. 6A and 6B), thereby directing exhaled breath toward the oral prong 122 as it is the only substantial exit.

The flaps 178 are preferably formed of a plastic material selected to be of suitable thickness to maintain their position when undisturbed, yet bend readily when pushed by an endoscope probe, and thus do not limit the actions of the medical personnel performing the endoscopy. However, the flaps 178 preferably close back around the endoscope probe, thus maintaining a substantially closed oral cavity volume, and allowing most of the exchange of gases to occur close to the opening 180 of the flexible barrier 176, which opening is close to the cut-away tip 124 of oral prong 122 from which capnographic sampling can be performed accurately. Additionally, the flaps 178 are preferably transparent, thus enabling medical personnel to see into the oral cavity during the endoscopy procedure.

Two attachment surfaces 182, each formed with a slit 184, extend horizontally outwardly from main body portion 152. Slits 184 are adapted to connect to a band which is place around the subject's head and is used to maintain the endoscopic bite block 150 firmly in position during the endoscopy procedure. Preferably, slits 184 are located above a horizontal centerline of main body portion 152, such that the connected band will tend to exert a stronger pull to the top of the main body portion 152, thus assisting in overcoming the subject's tendency to tilt the bite block 150 outward during the endoscopy procedure and in maintaining the bite block 150 upright in the subject's mouth.

Figure 9:
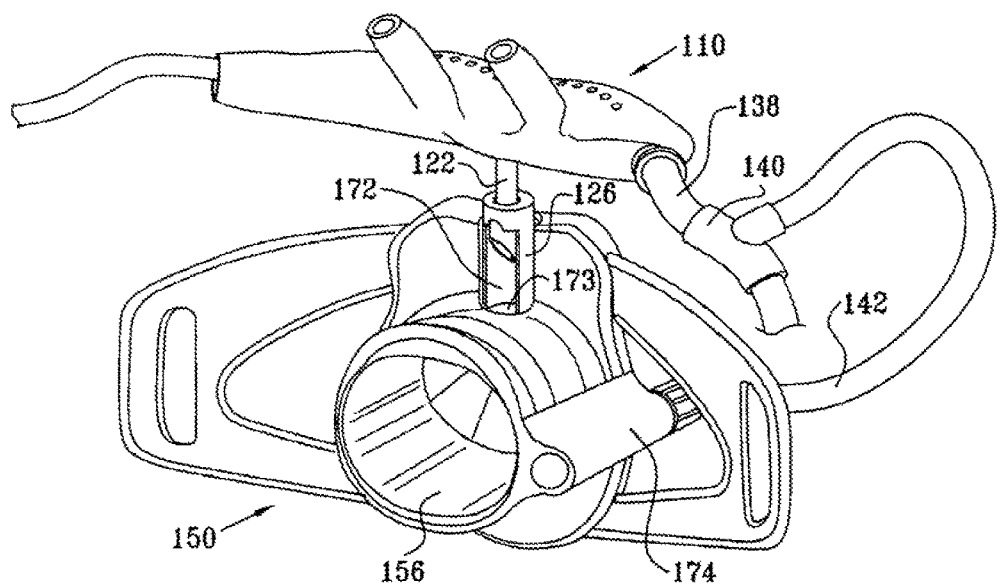
FIG. 9 is a simplified schematic illustration of the connection between the oral nasal cannula of FIGS. 6A and 6B and the endoscopic bite block of FIGS. 7A-8.

Reference is now made to FIG. 9, which is a simplified schematic illustration of the connection between the oral nasal sampling cannula of FIGS. 6A and 6B and the endoscopic bite block of FIGS. 7A-8.

As seen in FIG. 9, oral prong 122 of oral nasal sampling cannula 110 is accommodated within groove 172 of bite block 150, such that a bottom surface of oral breath directing element 126 engages transverse surface 173 of the groove 172. It is appreciated that transverse surface 173 is located below an inner surface of tubular portion 156 in order to ensure that air exhaled by the subject into tubular portion 156 will be directed toward groove 172 and oral prong 122.

Additionally, valve 144 (FIGS. 6A and 6B) of oral oxygen delivery tube 142 is accommodated in tubular portion 174 of endoscopic bite block 150, thereby opening the valve element and forming a fluid flow engagement between oxygen delivery tube 138 and tubular portion 174 of endoscopic bite block 150, which is in fluid flow engagement with the oral cavity of the subject.

Reference is now made to FIGS. 10A, 10B, 10C, 10D, 10E, 10F and 10G, which are pictorial illustrations of various stages of typical use of the endoscopic bite block assembly of FIGS. 6A-9.

Figure 10A:
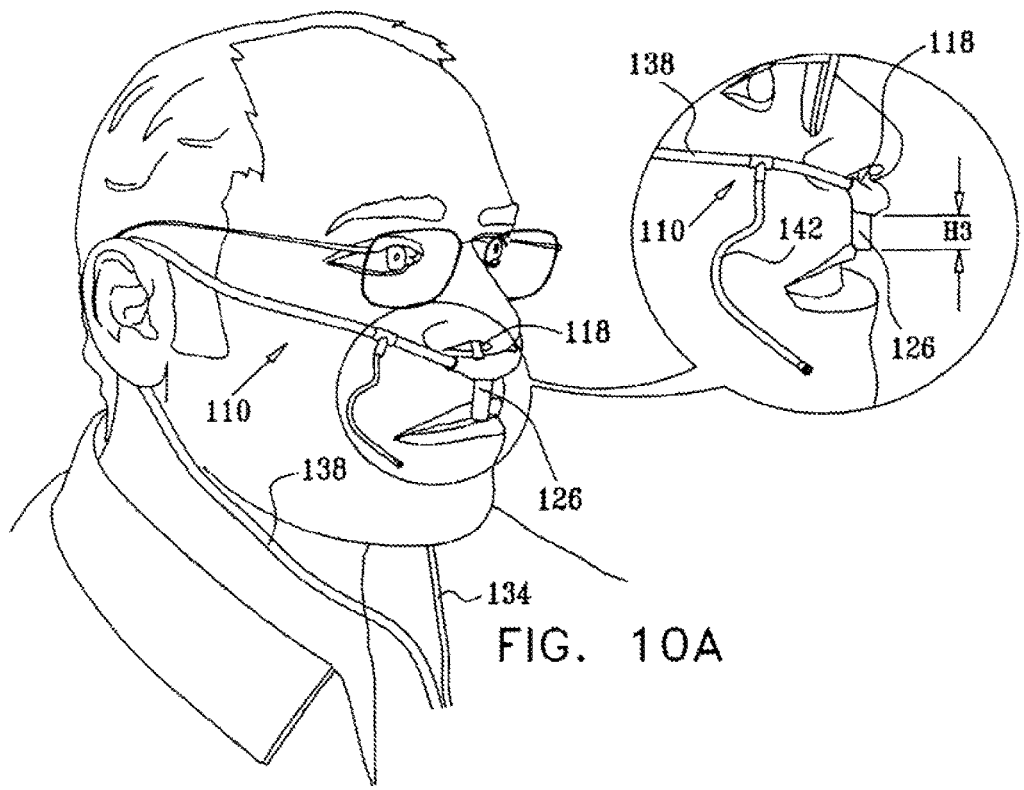
FIGS. 10A, 10B, 10C, 10D, 10E, 10F and 10G are pictorial illustrations of various stages of typical use of the endoscopic bite block assembly of FIGS. 5A-9.

As seen in FIG. 10A, the nasal prongs 118 of the oral nasal sampling cannula 110 are placed in the subjects nostrils, preferably before the subject is sedated. Preferably, the exhaled breath collection tube 134 and the oxygen delivery tube 138 are placed around the subject's ears, in order to ensure the stability of the oral nasal sampling cannula 110 on the subject's face. As seen in the enlarged portion of FIG. 10A, at this stage the oral breath-directing element 126 is in its retracted orientation, indicated by the length H3. At this stage, oral oxygen delivery tube 142 is not connected to the bite block 150 (FIGS. 7A-8).

Figure 10B:
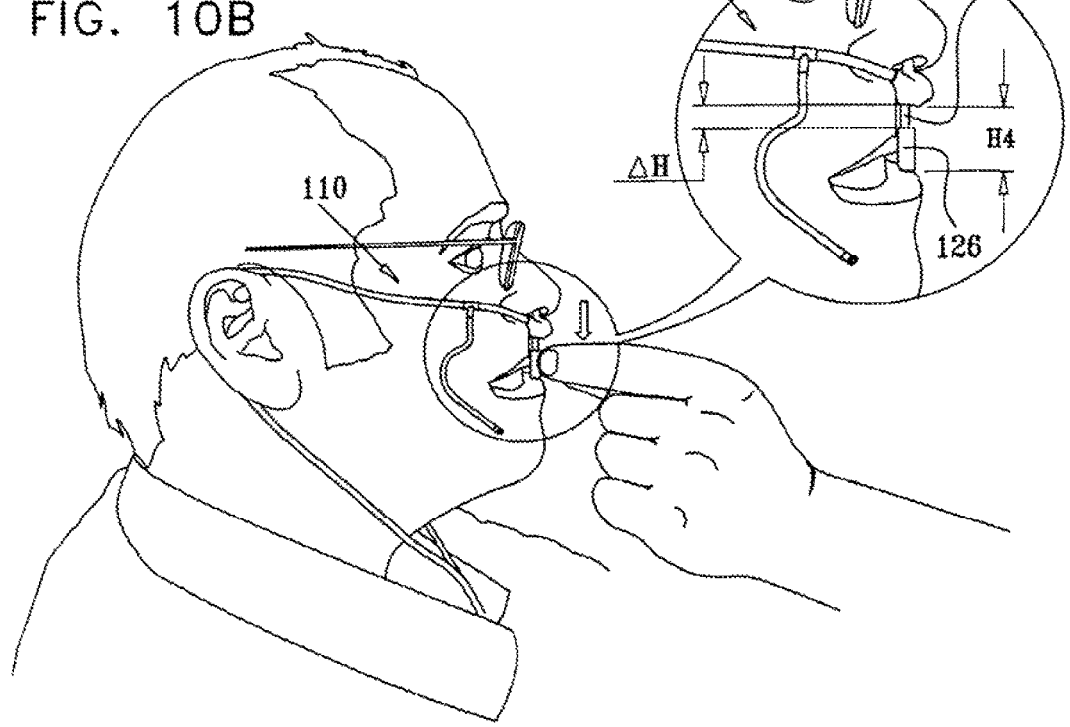

Turning to FIG. 10B, it is seen that the oral breath directing element 126 is extended to accommodate the facial dimensions of the subject, revealing part of oral prong 122. Preferably, the oral breath-directing element is moved down to a point in which a bottom end thereof is at the height of the top of the bottom lip of the subject, its new length being indicated by H4. This action is preferably preformed by medical personnel, but may alternatively be performed by the subject himself, a family member, or any other person.

Figure 10C:
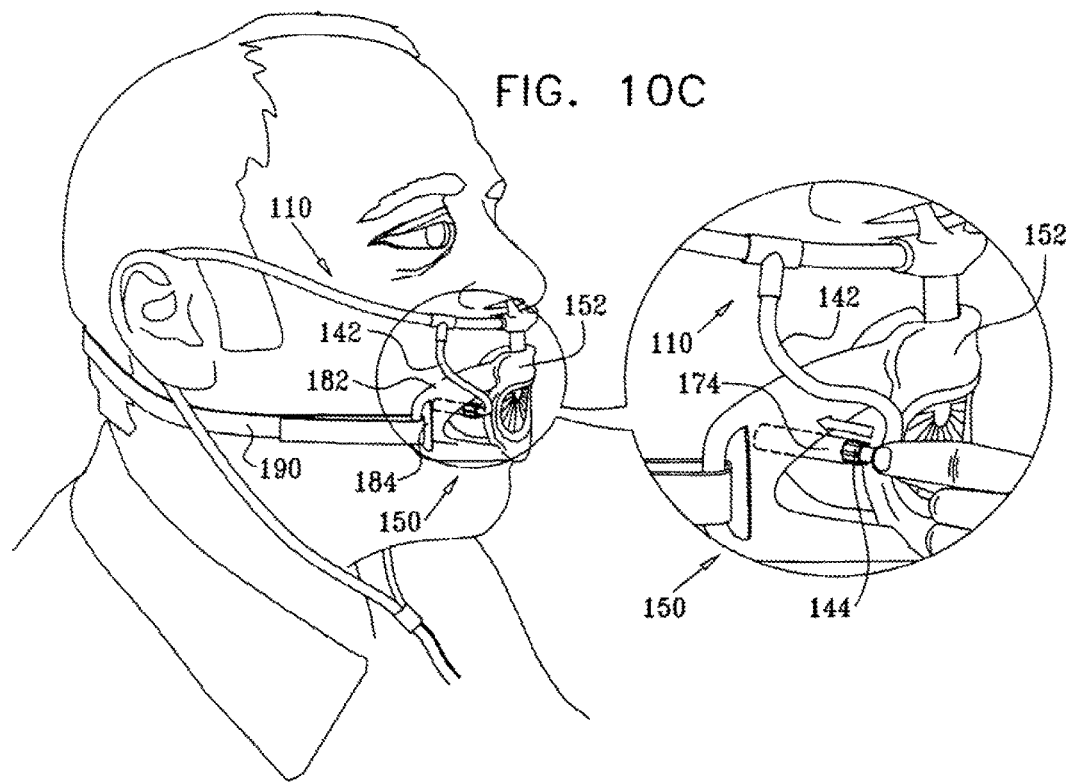

FIG. 10C illustrates the insertion of bite block 150 into the mouth of the subject, such that main body portion 152 engages the outer surface of the subject's lips and the tubular portion 156 (FIGS. 7A-8) is inside the subject's mouth. Additionally, valve 144 of oral oxygen delivery tube 142 is inserted, preferably by medical personnel, into tubular portion 174 of endoscopic bite block 150, as indicated by an arrow in the enlarged portion of FIG. 10C, thereby opening the valve and allowing passage of fluids from the oral oxygen delivery tube 142 into the oral cavity of the subject.

A strap, indicated by reference numeral 190, is attached to slits 184 of attachment surfaces 182 and is placed around the subject's head, thereby securing the bite block 150 in place.

This stage is preferably performed when the subject is sedated, but may alternatively be performed prior thereto.

Figure 10D:
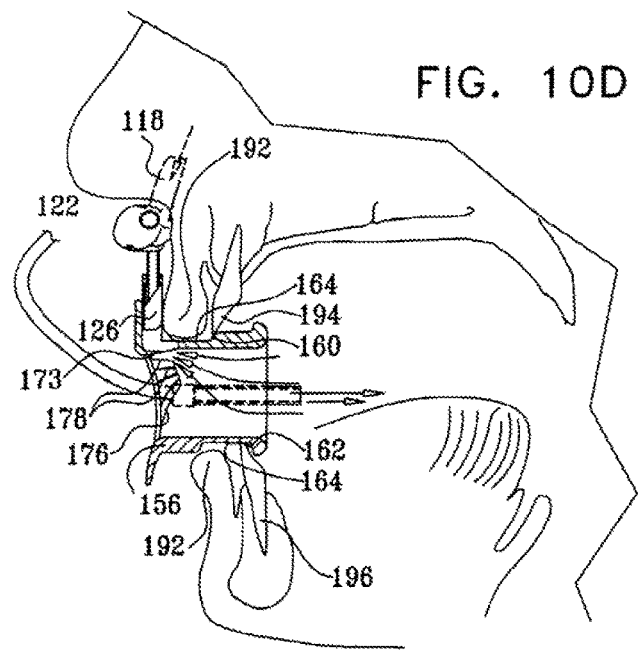

Turning to FIG. 10D, it is seen that air exhaled orally by the subject, indicated by arrows, passes through the bore of tubular portion 156, and is directed toward oral breath directing element 126 and oral prong 122 by the flaps 178 of flexible barrier 176. Air that is exhaled nasally by the subject passes through nasal prongs 118.

FIG. 10D illustrates the oral breath directing element 126 and the oral prong 122 being accommodated in groove 172, such that a bottom surface of the oral breath directing element 126 engages transverse surface 173 of groove 172. Additionally, if oral breath directing element 126 has been extended more than necessary for the facial features of the subject, the transverse surface 173 pushes the oral breath-directing element 126 back until it is optimally positioned. The lips of the subject, indicated by reference numeral 192 preferably engage jaw engagement recesses 164, and the top and bottom teeth of the subject, indicated by reference numerals 194 and 196 engage top and bottom teeth engagement surfaces 160 and 162, respectively.

Figure 10E:
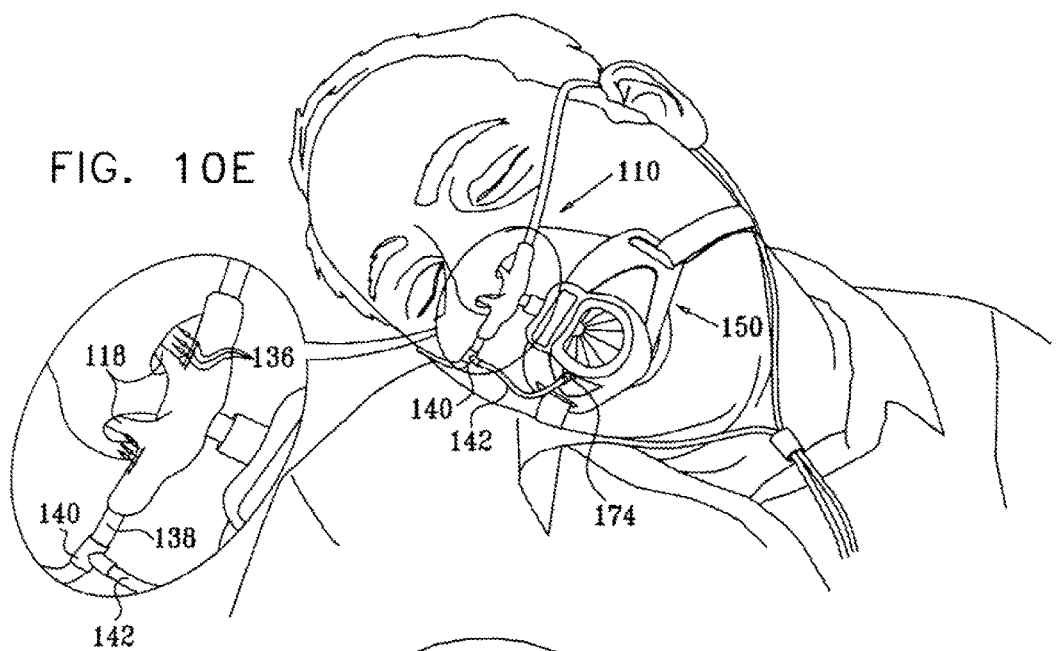

FIG. 10E illustrates the sedated subject, having the nasal prongs 118 of the oral nasal sampling cannula 110 in his nostrils and the endoscopic bite block 150 placed in his mouth and strapped to his head. Preferably, once the subject is sedated, oxygen is supplied to the nose of the subject via oxygen delivery openings 136 of oral nasal sampling cannula 110, and to the mouth of the subject via oral oxygen delivery tube 142 and tubular portion 174, as indicated by arrows. The oxygen is supplied to the oxygen delivery openings 136 via oxygen delivery bore 116 (FIGS. 6A and 6B) and to oral oxygen delivery tube 142 via oxygen delivery tube 138 and T-element 140.

Figure 10F:
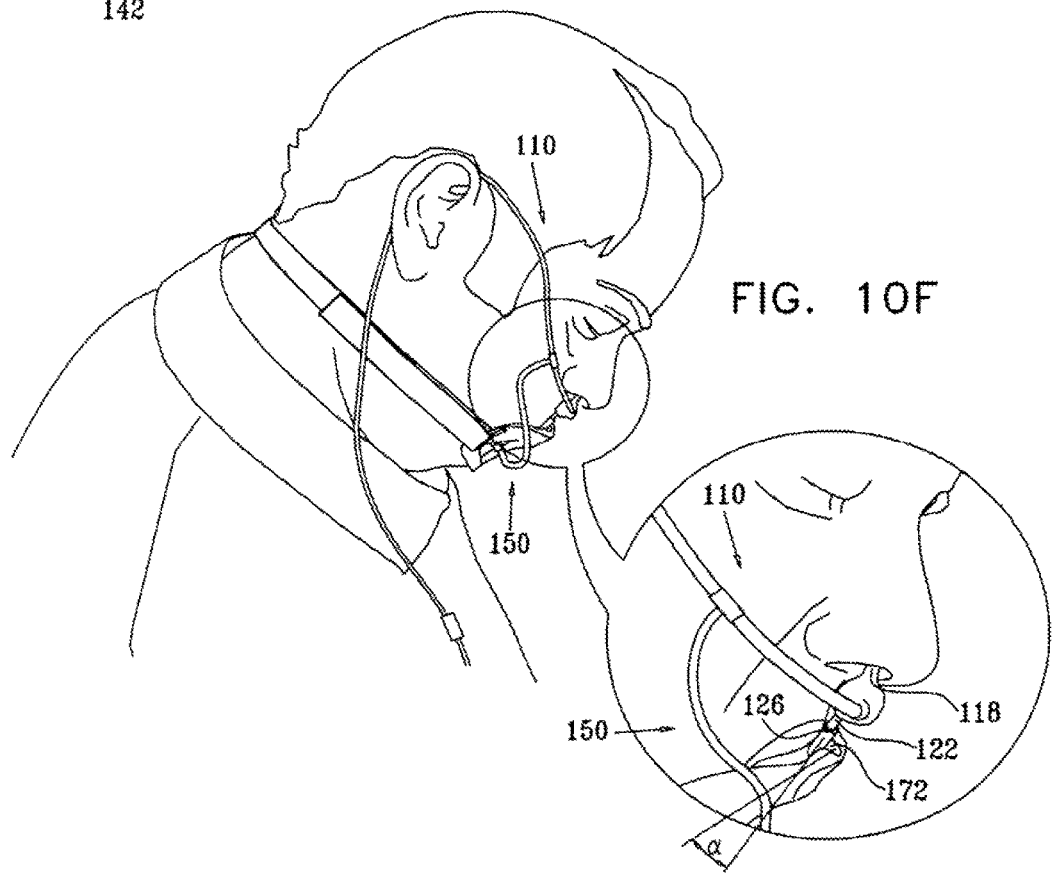

Turning to FIG. 10F, it is seen that when the subject is sedated, he tends to move or slump his head, thereby moving oral nasal sampling cannula 110 relative to bite block 150, as indicated by angle a in the enlarged portion of FIG. 10F. The feature of the present invention which provides oral nasal sampling cannula 110 which is physically separated from bite block 150 and the placement of oral breath directing element 126 and oral prong 122 within groove 172, ensure that even when the subject moves or slumps his head, the oral prong 122 and nasal prongs 118 will be maintained in their respective places, and accurate sampling will continue. Additionally, the placement of oral prong 122 within groove 172 provides a counter force to force applied by the subject's tongue to push at least the top portion of the bite block 150 out of the subject's mouth, thus ensuring accurate placement of the bite block.

Figure 10G:
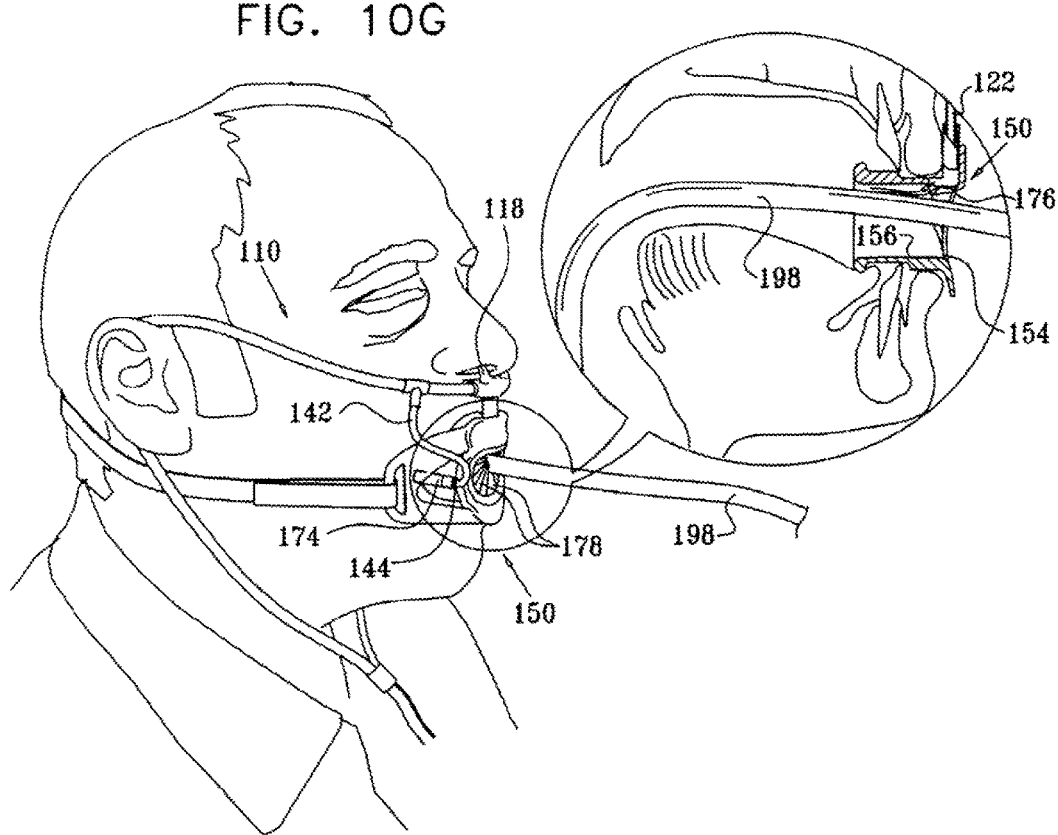

As seen in FIG. 10G, an endoscope probe 198 is inserted into the bore of tubular portion 156 of bite block 150, for performing the endoscopy procedure. During the insertion of endoscope probe 198 and its presence in the subject's mouth and pharynx, flaps 178 of flexible barrier 176 bend slightly inward to allow the passage of the endoscope probe 198, as seen with particular clarity in the enlarged portion of FIG. 10G. However, the central opening 154 of bite block 150 remains substantially closed by flaps 178, thereby separating the exhaled breath of the subject which is in bore of tubular portion 156 from the ambient air.

Additionally, the sampling may continue during the presence of the endoscope probe 198 in the pharynx of the subject, as the tubular portion 156 is of a slightly larger diameter than the central opening 154, thereby ensuring that medical personnel have the space defined by the difference between heights H2 and H1 (FIG. 8), as indicated by arrows in the enlarged portion of FIG. 10G.

It is appreciated that following the endoscopy, the bite block 150 may be removed from the subject's mouth, preferably by medical personnel. Prior to this stage, the valve 144 of oral oxygen delivery tube 142 is removed from tubular portion 174 thereby closing the valve and thus fully decoupling the oral nasal sampling cannula 110 from the endoscopic bite block 150. However, the sampling of exhaled breath through nasal prongs 118 which remain in the subject's nostrils and through oral prong 122 which remains near the subject's mouth, preferably continues until the subject has awaken from the sedation. This is necessary because the subject's breath must be monitored as long as the subject is sedated.

Figure 11A:
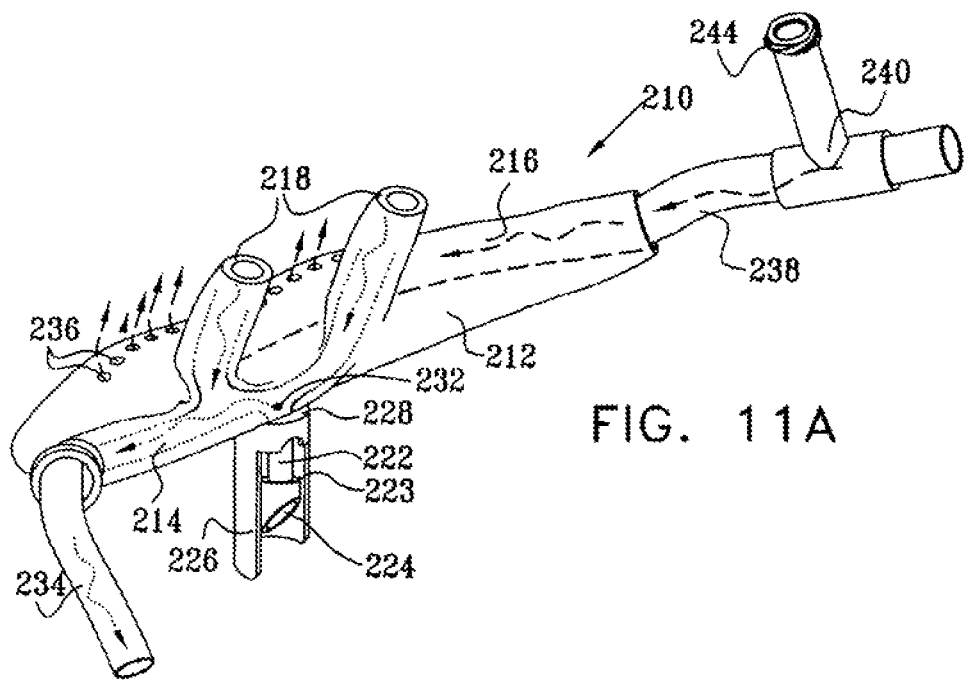
FIGS. 11A and 11B are simplified pictorial illustrations of an oral nasal cannula forming part of an endoscopic bite block assembly, constructed and operative in accordance with yet another preferred embodiment of the present invention, in retracted and extended orientations respectively.
Figure 11B:
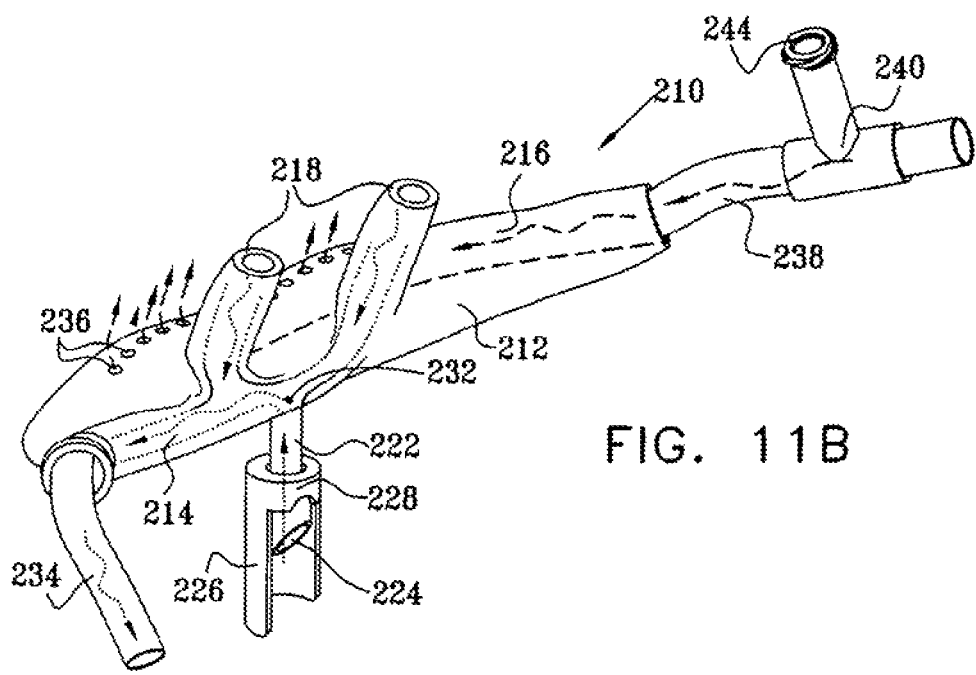

Reference is now made to FIGS. 11A and 11B, which are simplified pictorial illustrations of an oral nasal sampling cannula forming part of an endoscopic bite block assembly, constructed and operative in accordance with yet another preferred embodiment of the present invention, in retracted and extended orientations respectively.

FIGS. 11A and 11B show an oral nasal sampling cannula 210, which is adapted for collection of gases, such as carbon dioxide, exhaled by a subject, and for supplying oxygen to the subject.

The oral nasal sampling cannula 210 comprises a main body portion 212, having formed therein an exhaled breath collection bore 214 and an oxygen delivery bore 216. A pair of hollow nasal prongs 218, which are adapted for insertion into the nostrils of the subject, is integrally formed with the main body portion 212. A hollow oral prong 222, which is formed with a limiting rib 223 and a cut-away tip 224, is mounted onto a bottom surface of main body portion 212. An oral breath directing element 226, which is preferably in the shape of a cut-away tube, is slidably mounted onto oral prong 222 by a mounting portion 228, and positioning of the oral breath directing element 226 is limited by the limiting rib 223 of oral prong 222.

A channel formed in oral prong 222 is in fluid flow connection with channels formed in nasal prongs 218, thereby forming a single junction 232. Single junction 232 is in fluid flow communication with exhaled breath collection bore 214, which in turn is in fluid flow communication with an exhaled breath collection tube 234, which is adapted to be connected to a breath test analyzer or a capnograph (not shown), such as Microcap® which is commercially available from Oridion Medical LTD. of Jerusalem, Israel.

Main body portion 212 is formed with oxygen delivery openings 236, which are in fluid flow communication with oxygen delivery bore 216, which in turn is in fluid flow communication with an oxygen delivery tube 238. Alternatively, at least one nasal oxygen delivery prong, adapted for insertion into the subject's nostril, may be used instead of oxygen delivery openings 236. Oxygen delivery tube 238 is preferably formed with a T-element 240, preferably terminating at an end thereof in a normally closed valve element 244, which is preferably a luer valve. Oxygen delivery tube 238 is adapted to be connected to a source of oxygen (not shown).

Oxygen delivery tube 238 and exhaled breath collection tube 234 may optionally be placed around the ears of the subject, thereby stabilizing the oral nasal sampling cannula 210 on the subject's face, such that any movement of the subject will have negligible effect on the placement of the oral nasal sampling cannula 210.

It is appreciated that oral breath directing element 226 may be in a retracted orientation as shown in FIG. 11A, or in an extended orientation as shown in FIG. 11B, thereby allowing the oral nasal sampling cannula 210 to be suited to the facial dimensions of the subject, resulting in more efficient collection of exhaled breath.

Figure 12A:
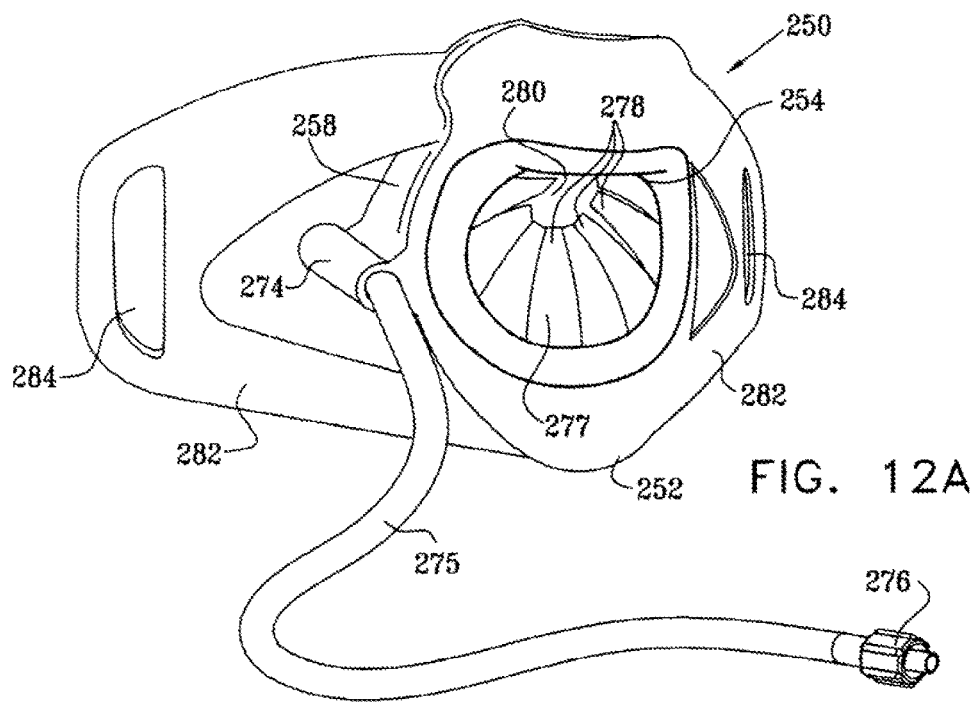
FIGS. 12A and 12B are front-view and rear-view simplified pictorial illustrations of an endoscopic bite block forming part of an endoscopic bite block assembly, constructed and operative in accordance with yet another preferred embodiment of the present invention.
Figure 12B:
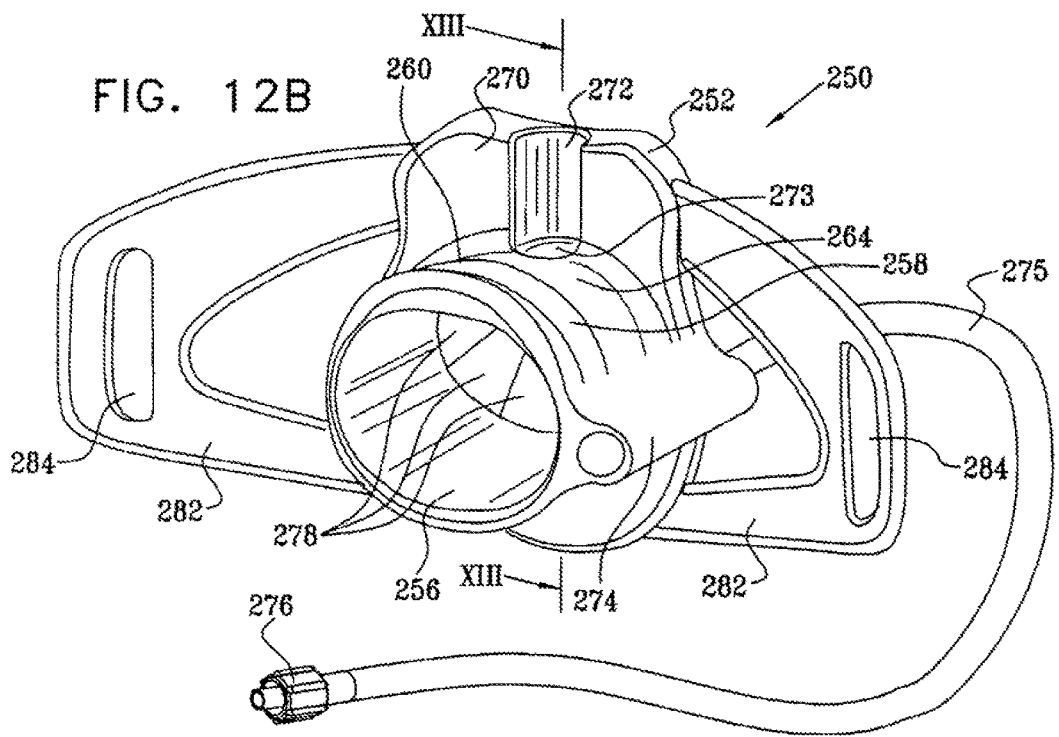
Figure 13:
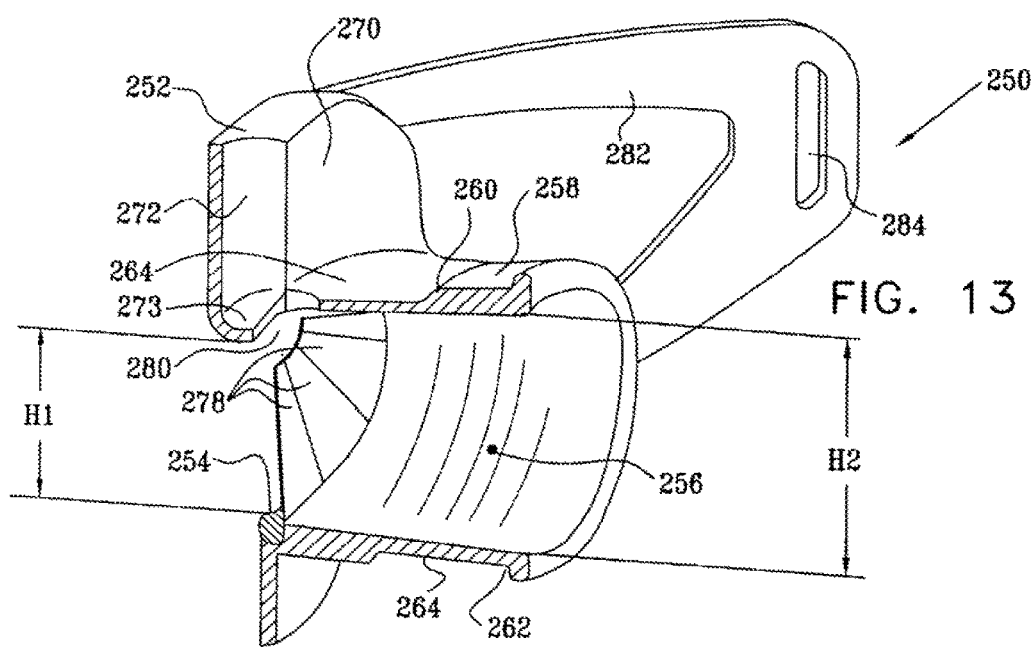
FIG. 13 is a simplified sectional pictorial illustration of the endoscopic bite block of FIGS. 12A and 12B, taken along sections lines XIII-XIII in FIG. 12B.

Reference is now made to FIGS. 12A and 12B, which are front-view and rear-view simplified pictorial illustrations of an endoscopic bite block forming part of an endoscopic bite block assembly constructed and operative in accordance with yet another preferred embodiment of the present invention and to FIG. 13, which is a simplified sectional pictorial illustration thereof.

FIGS. 12A, 12B and 13 show an endoscopic bite block 250, which is adapted to be inserted into the mouth of a subject while the subject is sedated, to ensure that the mouth of the subject is maintained open during the endoscopy process, and that the subject does not interfere with the process by biting on medical instruments used.

The endoscopic bite block 250 includes a main body portion 252, having formed therein a central opening 254. A hollow tubular portion 256 extends distally from main body portion 252, such that the opening of tubular portion 256 is an extension of central opening 254. Central opening 254 is of a first height, indicated by H1 in FIG. 13, which is typically 16 to 20 mm in bite blocks for adult use, which is the height required by medical personnel for performing an endoscopy. In order to ensure that during breath sampling, oral prong 222 of oral nasal sampling cannula 210 (FIGS. 11A and 11B) does not interfere with the space required by medical personnel for performing the endoscopy procedure, the height of tubular portion 256 is greater than the height H1 of central opening 254 as indicated by H2 in FIG. 13, and is typically 2 to 4 mm more than height H1 (18 to 24 mm).

An outer surface 258 of tubular portion 256 is formed with top and bottom teeth engagement surfaces 260 and 262, such that top teeth engagement surface 260 is relatively forward of bottom teeth engagement surface 262. This structure facilitates easy and accurate biting of the bite block 250 by a subject, as it is suited to the jaw morphology of a closed human mouth. Surface 258 is additionally formed with jaw engagement recesses 264, which are formed forwardly of teeth engagement surfaces 260 and 262, respectively.

A top inner surface 270 of main body portion 252 is formed with a longitudinal groove 272 having a transverse surface 273, which is adapted to accommodate oral prong 222 and oral breath directing element 226 of the oral nasal sampling cannula 210 (FIGS. 12A and 12B), as described with more detail hereinbelow with reference to FIG. 14.

A tubular portion 274 is formed on a side of outer surface 258 of tubular portion 256. Extending out of tubular portion 274 is an oral oxygen delivery tube 275 including a tip 276, which is adapted to engage valve 244 (FIGS. 11A and 11B), thereby supplying oxygen directly to the oral cavity of the subject. Preferably, tip 276 comprises a luer corresponding to luer valve 244. It is appreciated that tubular portion 274 is formed on outer surface 258 of tubular portion 256, in order to ensure that the oral oxygen delivery does not interfere with the procedure performed by the medical personnel.

A flexible barrier 277, preferably comprised of several flaps 278, is disposed within central opening 254, thereby substantially closing off the central opening and preventing dilution of exhaled breath by ambient air during sampling. An opening 280 is preferably maintained within flexible barrier 277, thereby ensuring a small part of central opening 254 remains open in order to enable the subject to inhale external air. The flexible barrier 277 ensures that a majority of the subject's orally exhaled breath will be directed toward oral prong 222 (FIGS. 11A and 11B) thereby ensuring accurate sampling of the subject's breath. Opening 280 is preferably placed at a top part of central opening 254 near the cut-away tip 224 of oral prong 222 (FIGS. 11A and 11B), thereby directing and amplifying exhaled breath toward the oral prong 222 as it is the only substantial exit.

The flaps 278 are preferably formed of a plastic material selected to be of suitable thickness to maintain their position when undisturbed, yet bend readily when pushed by an endoscope probe, and thus do not limit the actions of the medical personnel performing the endoscopy. However, the flaps 278 preferably close back around the endoscope probe, thus maintaining a substantially closed oral cavity volume, and allowing most of the exchange of gases to occur close to the opening 280 of flexible barrier 277, which opening is close to the cut-away tip 224 of oral prong 222 (FIGS. 11A and 11B) from which capnographic sampling can be performed accurately.

Additionally, the flaps 278 are preferably transparent, thus enabling medical personnel to see into the oral cavity during the endoscopy procedure.

Two attachment surfaces 282, each formed with a slit 284, extend horizontally outwardly from main body portion 252. Slits 284 are adapted to connect to a band which is placed around the subject's head and is used to maintain the endoscopic bite block 250 firmly in position during the endoscopy procedure. Preferably, slits 284 are located above a horizontal centerline of main body portion 252, such that the connected band will tend to exert a stronger pull to the top of the main body portion 252, thus assisting in overcoming the subject's tendency to tilt the bite block 250 outward during the endoscopy procedure and in maintaining the bite block 250 upright in the subject's mouth.

Figure 14:
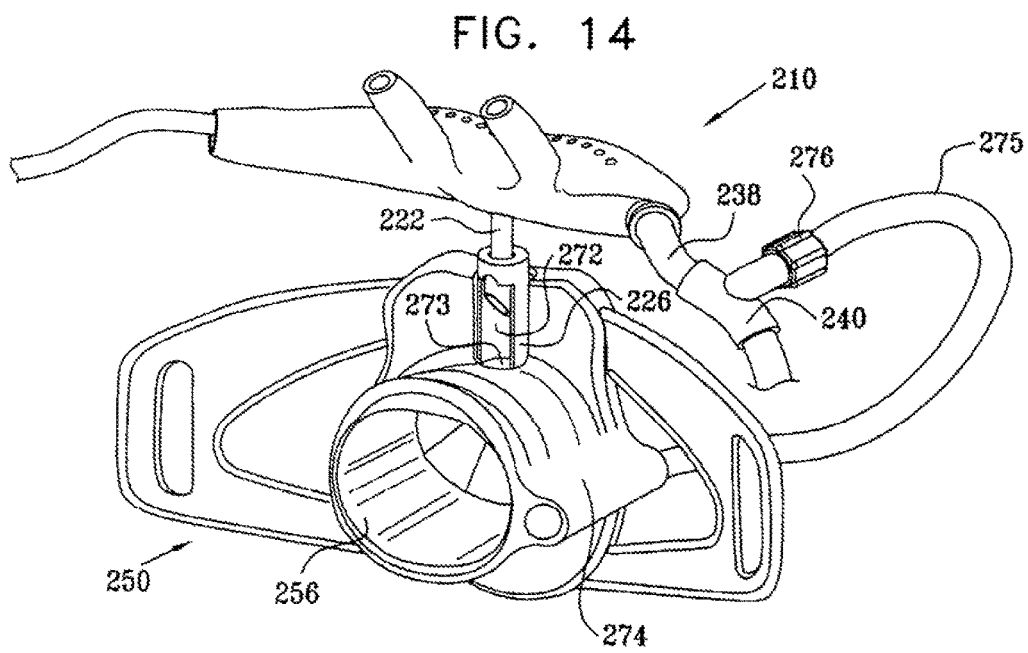
FIG. 14 is a simplified schematic illustration of the connection between the oral nasal cannula of FIGS. 11A and 11B and the endoscopic bite block of FIGS. 12A-13.

Reference is now made to FIG. 14, which is a simplified schematic illustration of the connection between the oral nasal sampling cannula of FIGS. 11A and 11B and the endoscopic bite block of FIGS. 12A-13.

As seen in FIG. 14, oral prong 222 of oral nasal sampling cannula 210 is accommodated within groove 272 of bite block 250, such that a bottom surface of oral breath directing element 226 engages transverse surface 273 of the groove 272. It is appreciated that transverse surface 273 is located below an inner surface of tubular portion 256 in order to ensure that air exhaled by the subject into tubular portion 256 will be directed toward groove 272 and oral prong 222.

Additionally, tip 276 of oral oxygen delivery tube 275 engages valve 244 (FIGS. 11A and 11B) of T-element 240 of oral nasal sampling cannula 210, thereby opening the valve 244 and forming a fluid flow engagement between oxygen delivery tube 238 and tubular portion 274 of endoscopic bite block 250, which is in fluid flow engagement with the oral cavity of the subject.

Reference is now made to FIGS. 15A, 15B, 15C, 15D, 15E, 15F and 15G, which are pictorial illustrations of various stages of typical use of the endoscopic bite block assembly of FIGS. 11A-14.

Figure 15A:
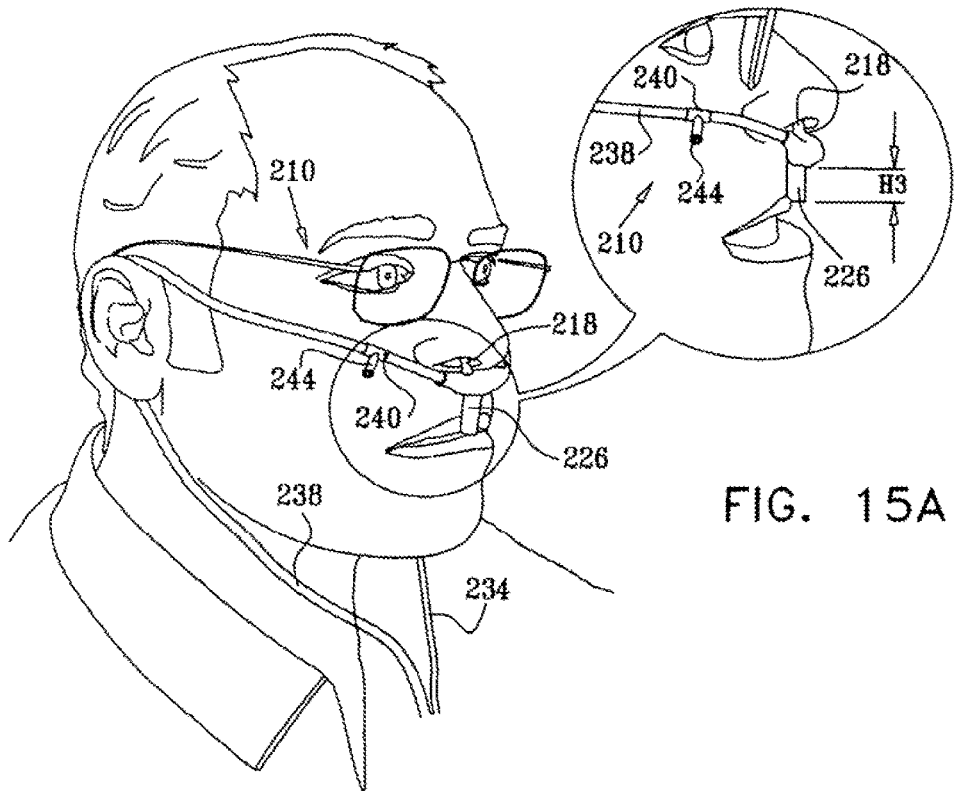
FIGS. 15A, 15B, 15C, 15D, 15E, 15F and 15G are pictorial illustrations of various stages of typical use of the endoscopic bite block assembly of FIGS. 11A-14.

As seen in FIG. 15A, the nasal prongs 218 of the oral nasal sampling cannula 210 are placed in the subjects nostrils, preferably before the subject is sedated. Preferably, the exhaled breath collection tube 234 and the oxygen delivery tube 238 are placed around the subject's ears, in order to ensure the stability of the oral nasal sampling cannula 210 on the subject's face. As seen in the enlarged portion of FIG. 15A, at this stage the oral breath-directing element 226 is in its retracted orientation, indicated by the length H3.

At this stage, oral oxygen delivery tube 275 (FIGS. 12A-13) is not connected to the T-element 240 of oral nasal sampling cannula 210. However, even if oxygen is supplied to oral nasal sampling cannula 210 via oxygen delivery tube 238, there is no oxygen leakage, as the T-element 240 is sealed by valve 244.

Figure 15B:
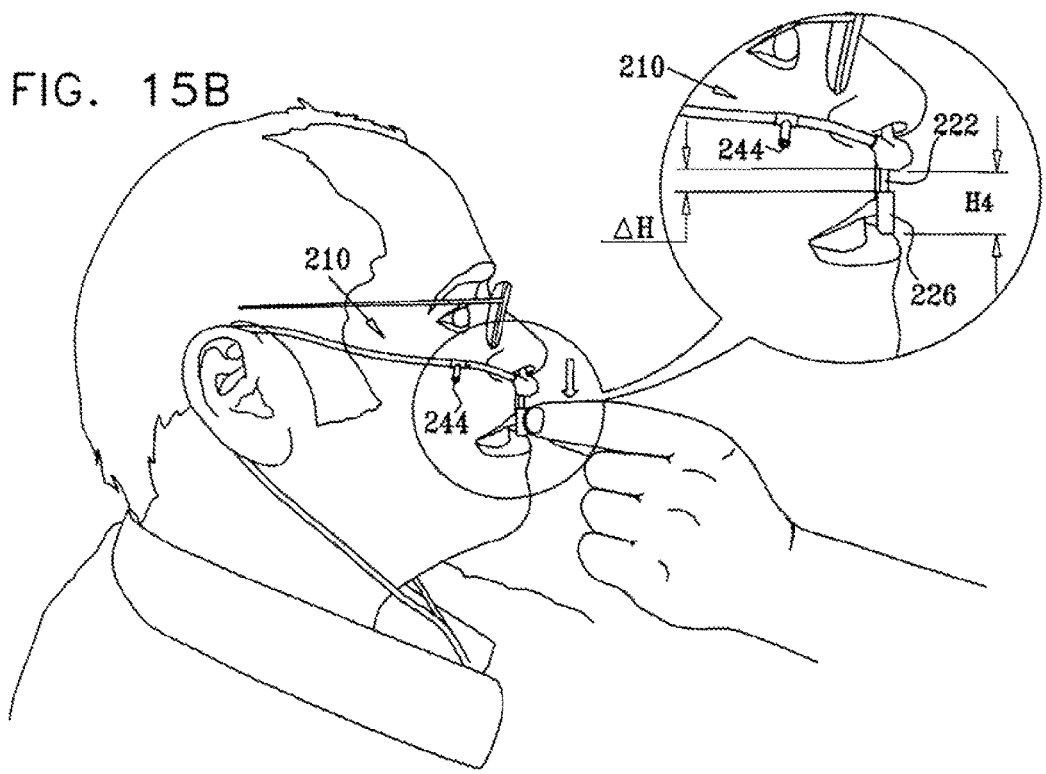

Turning to FIG. 15B it is seen that the oral breath directing element 226 is extended to accommodate the facial dimensions of the subject, revealing part of oral prong 222. Preferably, the oral breath-directing element 226 is moved down to a point in which a bottom end thereof is at the height of the top of the bottom lip of the subject, its new length being indicated by H4. This action is preferably preformed by medical personnel, but may alternatively be performed by the subject himself, a family member, or any other person.

Figure 15C:
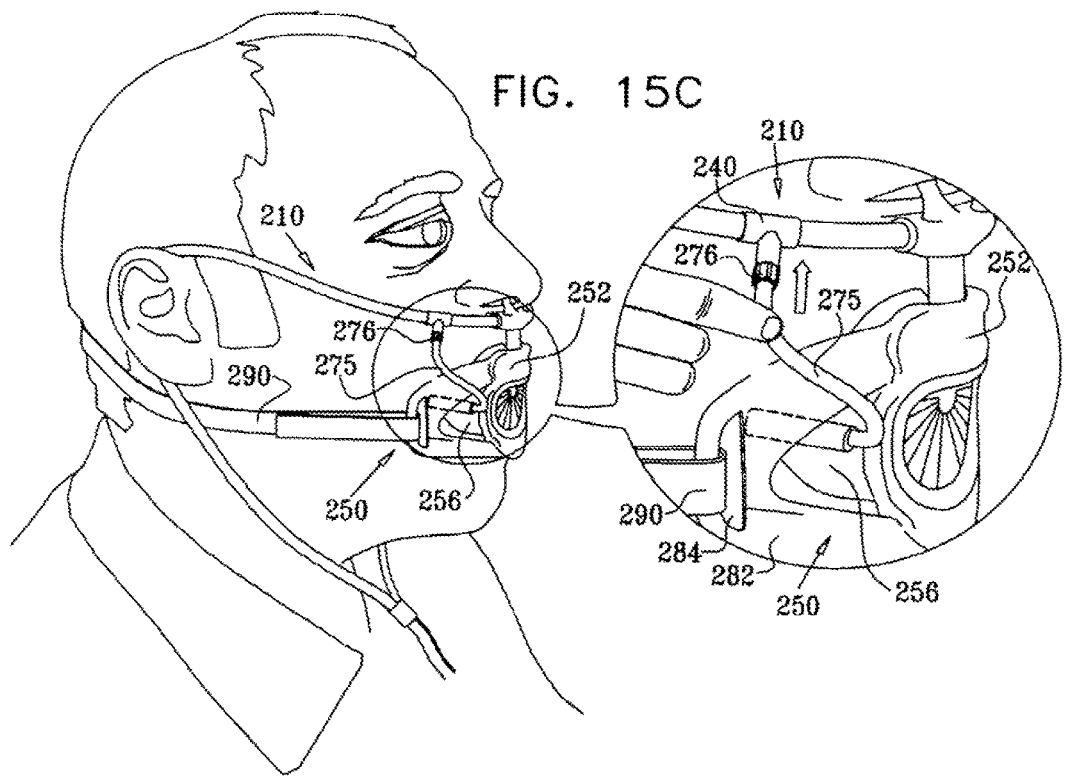

FIG. 15C illustrates the insertion of bite block 250 into the mouth of the subject, such that main body portion 252 engages the outer surface of the subject's lips and the tubular portion 256 is inside the subject's mouth. Additionally, tip 276 of oral oxygen delivery tube 275 is inserted, preferably by medical personnel, into valve 244 of T-element 240 of oral nasal sampling cannula 210, as indicated by an arrow in the enlarged portion of FIG. 15C, thereby opening the valve 244.

A strap, indicated by reference numeral 290, is attached to slits 284 of attachment surfaces 282 and is placed around the subject's head, thereby securing the bite block 250 in place. This stage is preferably performed when the subject is sedated, but may alternatively be performed prior thereto.

Figure 15D:
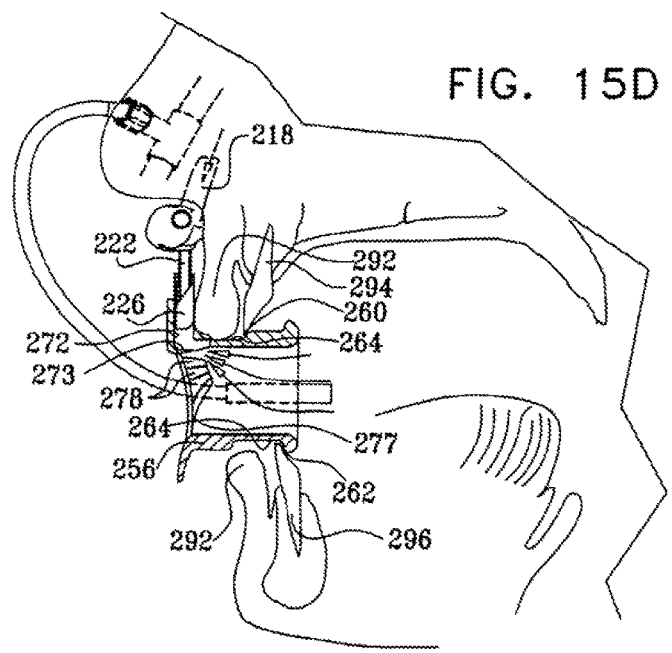

Turning to FIG. 15D, it is seen that air exhaled orally by the subject, indicated by arrows, passes through the bore of tubular portion 256, and is directed toward oral breath directing element 226 and oral prong 222 by the flaps 278 of flexible barrier 277. Air that is exhaled nasally by the subject passes through nasal prongs 218.

FIG. 15D illustrates the oral breath directing element 226 and the oral prong 222 being accommodated in groove 272, such that a bottom surface of the oral breath directing element 226 engages transverse surface 273 of groove 272. Additionally, if oral breath directing element 226 has been extended more than necessary for the facial features of the subject, the transverse surface 273 pushes the oral breath-directing element 226 back until it is optimally positioned. The lips of the subject, indicated by reference numeral 292 preferably engage jaw engagement recesses 264, and the top and bottom teeth of the subject, indicated by reference numerals 294 and 296 engage top and bottom teeth engagement surfaces 260 and 262, respectively.

Figure 15E:
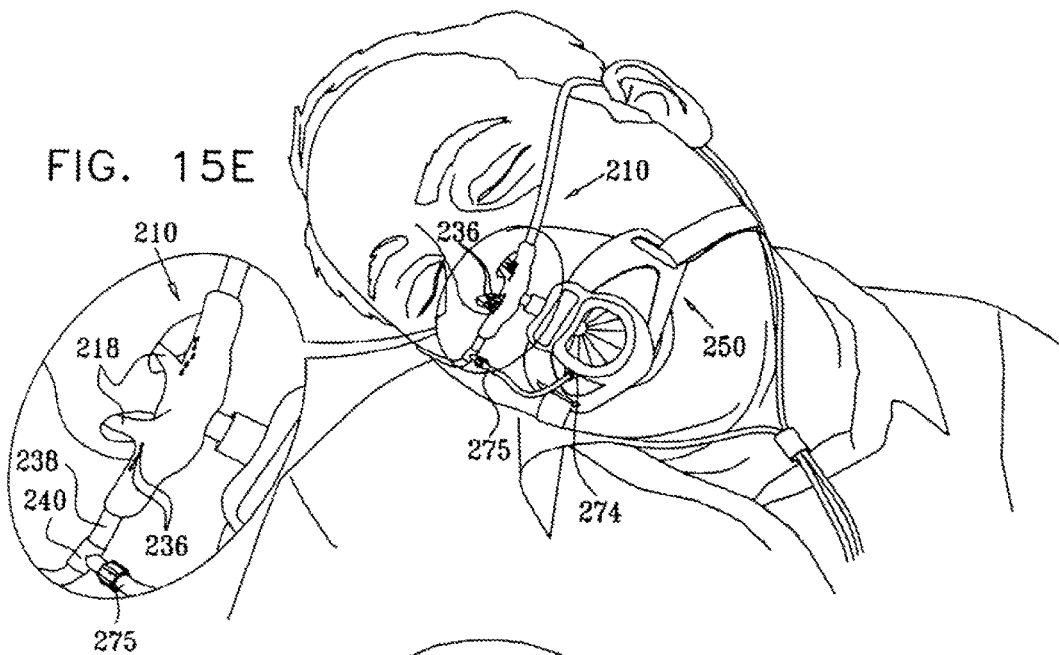

FIG. 15E illustrates the sedated subject, having the nasal prongs 218 of the oral nasal sampling cannula 210 in his nostrils and the endoscopic bite block 250 placed in his mouth and strapped to his head. Preferably, once the subject is sedated, oxygen is supplied to the nose of the subject via oxygen delivery openings 236 of oral nasal sampling cannula 210, and to the mouth of the subject via oral oxygen delivery tube 275 and tubular portion 274, as indicated by arrows. The oxygen is supplied to the oxygen delivery openings 236 via oxygen delivery bore 216 (FIGS. 11A and 11B) and to oral oxygen delivery tube 275 via oxygen delivery tube 238 and T-element 240.

Figure 15F:
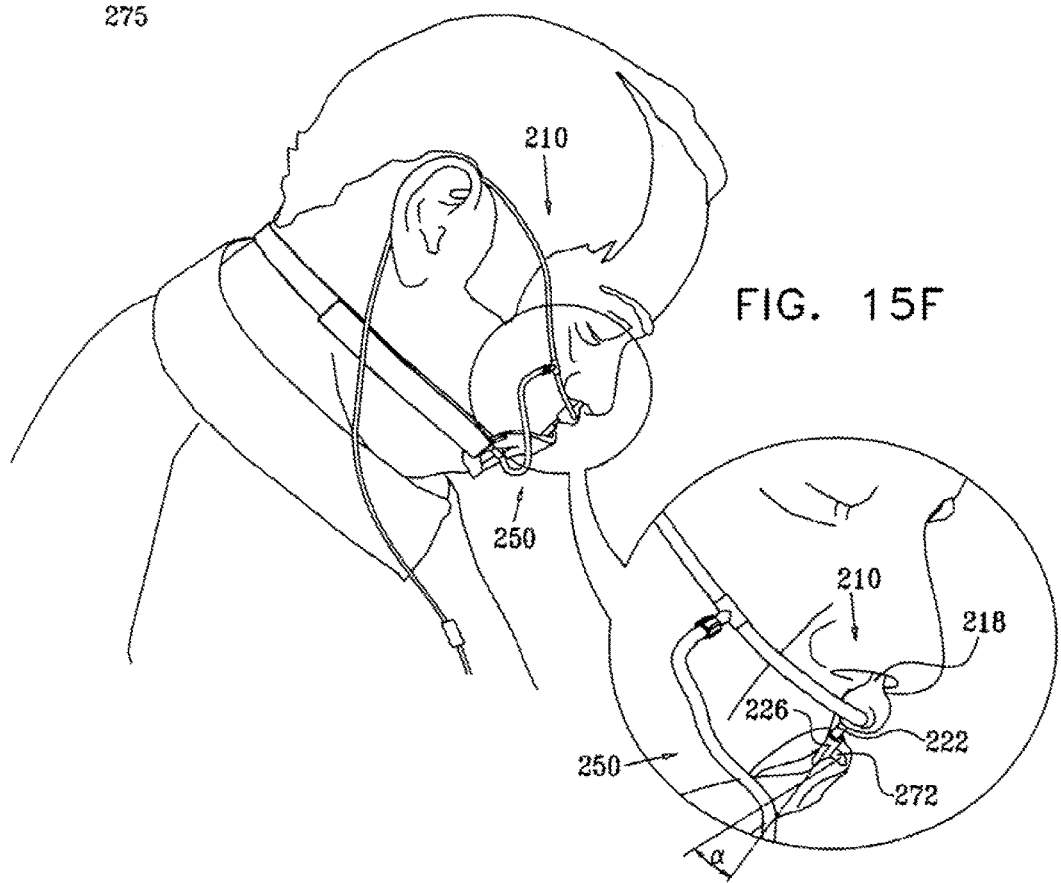

Turning to FIG. 15F, it is seen that when the subject is sedated, he tends to move or slump his head, thereby moving oral nasal sampling cannula 210 relative to bite block 250, as indicated by angle a in the enlarged portion of FIG. 15F. The feature of the present invention which provides oral nasal sampling cannula 210 which is physically separated from bite block 250 and the placement of oral breath directing element 226 and oral prong 222 within groove 272, ensure that even when the subject moves or slumps his head, the oral prong 222 and nasal prongs 218 will be maintained in their respective places, and accurate sampling will continue. Additionally, the placement of oral prong 222 within groove 272 provides a counter force to force applied by the subject's tongue to push at least the top portion of the bite block 250 out of the subject's mouth, thus ensuring accurate placement of the bite block.

Figure 15G:
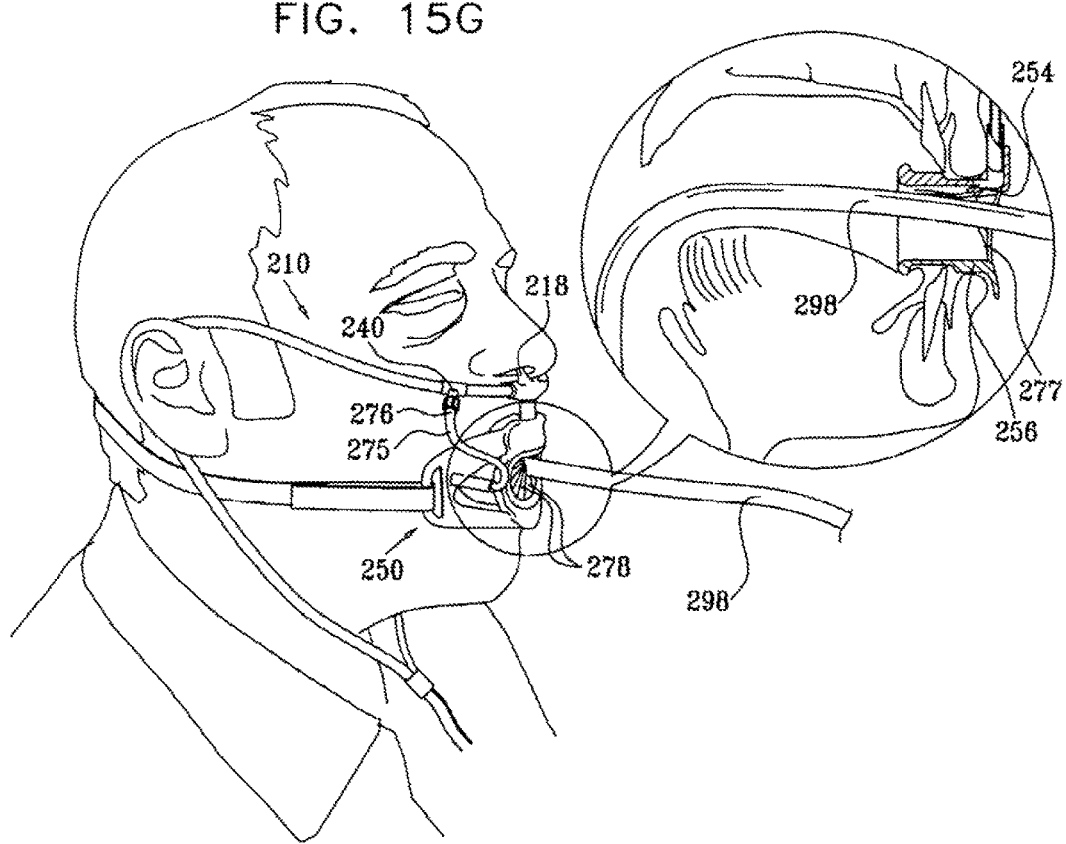

As seen in FIG. 15G, an endoscope probe 298 is inserted into the bore of tubular portion 256 of bite block 250, for performing the endoscopy procedure. During the insertion of endoscope probe 298 and its presence in the subject's mouth and pharynx, flaps 278 of flexible barrier 277 bend slightly inward to allow the passage of the endoscope probe 298, as seen with particular clarity in the enlarged portion of FIG. 15G. However, the central opening 254 of bite block 250 remains substantially closed by flaps 278, thereby separating the exhaled breath of the subject which is in the bore of tubular portion 256 from the ambient air.

Additionally, the sampling may continue during the presence of the endoscope probe 298 in the pharynx of the subject, as the tubular portion 256 is of a slightly larger diameter than the central opening 254, thereby ensuring that medical personnel have the space defined by the difference between heights H2 and H1 (FIG. 13), as indicated by arrows in the enlarged portion of FIG. 15G.

It is appreciated that following the endoscopy the bite block 250 may be removed from the subject's mouth, preferably by medical personnel. Prior to this stage, the tip 276 of oral oxygen delivery tube 275 is removed from valve 244 (FIGS. 11A and 11B) of T-element 240, thereby closing the valve and fully decoupling the oral nasal sampling cannula 210 from the endoscopic bite block 250. However, the sampling of exhaled breath through nasal prongs 218 which remain in the subject's nostrils and through oral prong 222 which remains near the subject's mouth, preferably continues until the subject has awaken from the sedation. This is necessary because the subject's breath must be monitored as long as the subject is sedated.

It is appreciated by persons skilled in the art that the present invention is not limited by what has been particularly shown and described hereinabove. Rather the scope of the present invention includes both combinations and sub-combinations of various features described hereinabove as well as variations and modifications thereto which would occur to a person of skill in the art upon reading the above description and which are not in the prior art.

The invention claimed is:

1. A bite block assembly comprising:
    a body comprising a first outer surface, an inner surface, and a first opening disposed on the outer surface, wherein the inner surface is configured to contact at least a portion of a patient's mouth;
    a hollow tubular portion extending away from the inner surface between the first opening and a second opening and configured to be inserted into the patient's mouth, wherein the hollow tubular portion terminates at the second opening;
    a groove extending between an outer periphery of the body and a third opening disposed on a second outer surface of the hollow tubular portion, wherein the groove is orthogonal to the hollow tubular portion; and
    an oxygen delivery channel disposed on the body and adjacent to the hollow tubular portion, wherein the oxygen delivery channel is configured to supply oxygen to the patient.

2. The bite block assembly of claim 1, comprising a cannula configured to collect exhaled breath for capnographic monitoring and to deliver oxygen to the patient, wherein the cannula comprises an oxygen delivery bore, an oxygen supply tube, an exhaled breath collection bore, an oral prong, and at least one nasal prong.

3. The bite block assembly of claim 2, wherein the oxygen supply tube is fluidly coupled to the oxygen delivery bore and the oxygen delivery channel.

4. The bite block assembly of claim 2, wherein the oral prong is disposed within the groove.

5. The bite block assembly of claim 2, wherein the oxygen delivery channel is fluidly coupled to an oral oxygen delivery tube, and wherein a tip of the oral oxygen delivery tube is configured to be coupled to a valve disposed on an end of the oxygen supply tube.

6. The bite block assembly of claim 1, wherein the groove terminates in a transverse surface adjacent to the third opening, and wherein the transverse surface is located below a second inner surface of the hollow tubular portion.

7. The bite block assembly of claim 1, wherein the second outer surface of the hollow tubular portion comprises a recess along a circumferential portion of the hollow tubular portion, wherein the recess is configured to engage the patient's teeth when the hollow tubular portion is inserted into the patient's mouth.

8. The bite block assembly of claim 1, wherein the body comprises a pair of attachment surfaces, and wherein each attachment surface comprises a slit configured to receive a band for securing the bite block to the patient.

9. A bite block assembly comprising:
a cannula configured to collect exhaled breath for capnographic monitoring and to deliver oxygen to a patient, wherein the cannula comprises an oxygen delivery bore and an oxygen supply tube;
a body comprising a first outer surface, an inner surface, and a first opening disposed on the outer surface, wherein the inner surface is configured to contact at least a portion of the patient's mouth;
a hollow tubular portion extending from the first opening and terminating at a second opening, wherein the hollow tubular portion forms a continuous passageway between the first opening and the second opening, and wherein the hollow tubular portion is configured to be inserted into the patient's mouth;
a groove formed along the inner surface of the body and orthogonal to the hollow tubular portion, wherein the groove is configured to receive the oxygen delivery bore; and
an oxygen delivery channel disposed on the body and adjacent to the hollow tubular portion, wherein the oxygen delivery channel is configured to couple to the cannula.

10. The bite block assembly of claim 9, wherein the cannula comprises an oral prong configured to be inserted into the groove.

11. The bite block assembly of claim 10, wherein the cannula comprises at least one nasal prong, and wherein the at least one nasal prong is fluidly coupled to the oral prong and the hollow tubular portion.

12. The bite block assembly of claim 11, wherein the cannula comprises an exhaled breath collection bore and an exhaled breath collection tube, and wherein the exhaled breath collection bore and the exhaled breath collection tube are fluidly coupled to the oral prong and the at least one nasal prong and configured direct exhaled breath from the patient to a capnograph.

13. The bite block assembly of claim 9, wherein the oxygen delivery channel is fluidly coupled to an oral oxygen delivery tube of the cannula, and wherein the oral oxygen delivery tube is configured to be coupled to the oxygen supply tube.

14. The bite block assembly of claim 9, wherein the hollow tubular portion comprises a third opening, and wherein a portion of the groove extends through the third opening and terminates in a transverse surface below a second inner surface of the hollow tubular portion.

15. The bite block assembly of claim 9, wherein a second outer surface of the hollow tubular portion comprises a recess along a portion of a circumference of the hollow tubular portion, and wherein the recess is configured to engage the patient's teeth when the hollow tubular portion is inserted into the patient's mouth.

16. The bite block assembly of claim 9, wherein the body comprises a pair of attachment surfaces, and wherein each attachment surface comprises a slit configured to receive a band for securing the bite block to the patient.

17. A bite block comprising:
a body comprising a first outer surface and a first inner surface, wherein the first inner surface is configured to contact at least a portion of a patient's mouth;
a first opening disposed on the first outer surface of the body;
a hollow tubular portion disposed between the first opening and terminating in a second opening, wherein the hollow tubular portion forms a continuous passageway between the first and second openings, and wherein the hollow tubular portion is configured to be inserted into the patient's mouth;
a groove formed on the first inner surface adjacent to the hollow tubular portion, wherein the groove is orthogonal to the hollow tubular portion; and
an oxygen delivery channel disposed on the body and adjacent to the hollow tubular portion, wherein the oxygen delivery channel is configured to supply oxygen to the patient's mouth.

18. The bite block of claim 17, wherein the hollow tubular portion comprises a third opening, and wherein a portion of the groove extends through the third opening and terminates in a transverse surface below a second inner surface of the hollow tubular portion.

19. The bite block of claim 17, wherein a second outer surface of the hollow tubular portion comprises a recess along a portion of a circumference of the hollow tubular portion, and wherein the recess is configured to engage the patient's teeth when the hollow tubular portion is inserted into the patient's mouth.

20. The bite block of claim 17, wherein the body comprises a pair of attachment surfaces, and wherein each attachment surface comprises a slit configured to receive a band for securing the bite block to the patient.

* * * * *